(12) United States Patent
Hassel

(10) Patent No.: US 11,083,614 B2
(45) Date of Patent: Aug. 10, 2021

(54) ANKLE-FOOT ORTHOSIS AND METHOD OF MANUFACTURE

(71) Applicant: SpringStep AFO, Inc., Denver, CO (US)

(72) Inventor: Mark Howard Hassel, Thornton, CO (US)

(73) Assignee: SpringStep AFO, Inc., Denver, CO (US)

( * ) Notice: Subject to any disclaimer, the term of this patent is extended or adjusted under 35 U.S.C. 154(b) by 984 days.

(21) Appl. No.: 15/448,357

(22) Filed: Mar. 2, 2017

(65) Prior Publication Data

US 2017/0196720 A1   Jul. 13, 2017

Related U.S. Application Data

(63) Continuation-in-part of application No. 14/859,025, filed on Sep. 18, 2015, now Pat. No. 10,485,688.

(60) Provisional application No. 62/052,615, filed on Sep. 19, 2014.

(51) Int. Cl.
*A61F 5/00* (2006.01)
*A61F 5/01* (2006.01)

(52) U.S. Cl.
CPC ................... *A61F 5/0113* (2013.01)

(58) Field of Classification Search
CPC ........ A61F 5/14; A61F 5/0127; A61F 5/0113; A61F 5/0111; A61H 2201/10; A61H 2201/164; A61H 2201/165; A61H 2201/5015; A61H 220/5061; A61H 2201/5064; A61H 2205/106; A61H 3/00

USPC ............................................ 602/27, 28, 6, 7
See application file for complete search history.

(56) References Cited

U.S. PATENT DOCUMENTS

| | | | | |
|---|---|---|---|---|
| 6,146,344 A | * | 11/2000 | Bader | A61F 5/0111 602/12 |
| 6,146,349 A | * | 11/2000 | Rothschild | A61F 5/0111 602/27 |
| 6,887,213 B2 | * | 5/2005 | Smits | A61F 5/0111 602/27 |
| 6,945,947 B2 | * | 9/2005 | Ingimundarson | A61F 5/0113 128/882 |
| 7,077,818 B2 | * | 7/2006 | Ingimundarson | A61F 5/0113 128/882 |
| 7,618,387 B2 | * | 11/2009 | Buethorn | A61F 5/14 128/882 |
| 7,766,851 B2 | * | 8/2010 | Lindh | A61F 5/0113 602/28 |
| 8,480,604 B2 | * | 7/2013 | Messer | A61F 5/0111 602/27 |
| 2006/0084899 A1 | * | 4/2006 | Verkade | A61F 5/0111 602/27 |
| 2007/0038169 A1 | * | 2/2007 | Alon | A61F 5/0111 602/27 |
| 2007/0073202 A1 | * | 3/2007 | Bader | A61F 5/0111 602/8 |

(Continued)

*Primary Examiner* — Kim M Lewis
(74) *Attorney, Agent, or Firm* — Polsinelli PC

(57) ABSTRACT

An ankle-foot orthosis for a lower leg, ankle, and foot of a patient, the ankle-foot orthosis including: a foot plate; a calf-cuff member; and a strut member extending between the foot plate and the calf-cuff member, the strut member coupling to an arch region of a medial side of the foot plate and a posterior side of the calf-cuff member, the strut member being formed from layers of carbon fiber and at least one layer of a thermoplastic material.

12 Claims, 19 Drawing Sheets

(56) References Cited

U.S. PATENT DOCUMENTS

| | | | | |
|---|---|---|---|---|
| 2012/0238928 A1* | 9/2012 | Buethorn | .................. | A61F 5/14 |
| | | | | 602/27 |
| 2014/0257162 A1* | 9/2014 | Falkenman | .............. | A43B 7/20 |
| | | | | 602/27 |
| 2015/0150709 A1* | 6/2015 | Ljubimir | ............... | A61F 5/0127 |
| | | | | 602/5 |
| 2015/0305911 A1* | 10/2015 | Schroeder | ............. | A61F 5/0127 |
| | | | | 602/28 |
| 2017/0216071 A1* | 8/2017 | Bader | .................. | A61F 5/0113 |

* cited by examiner

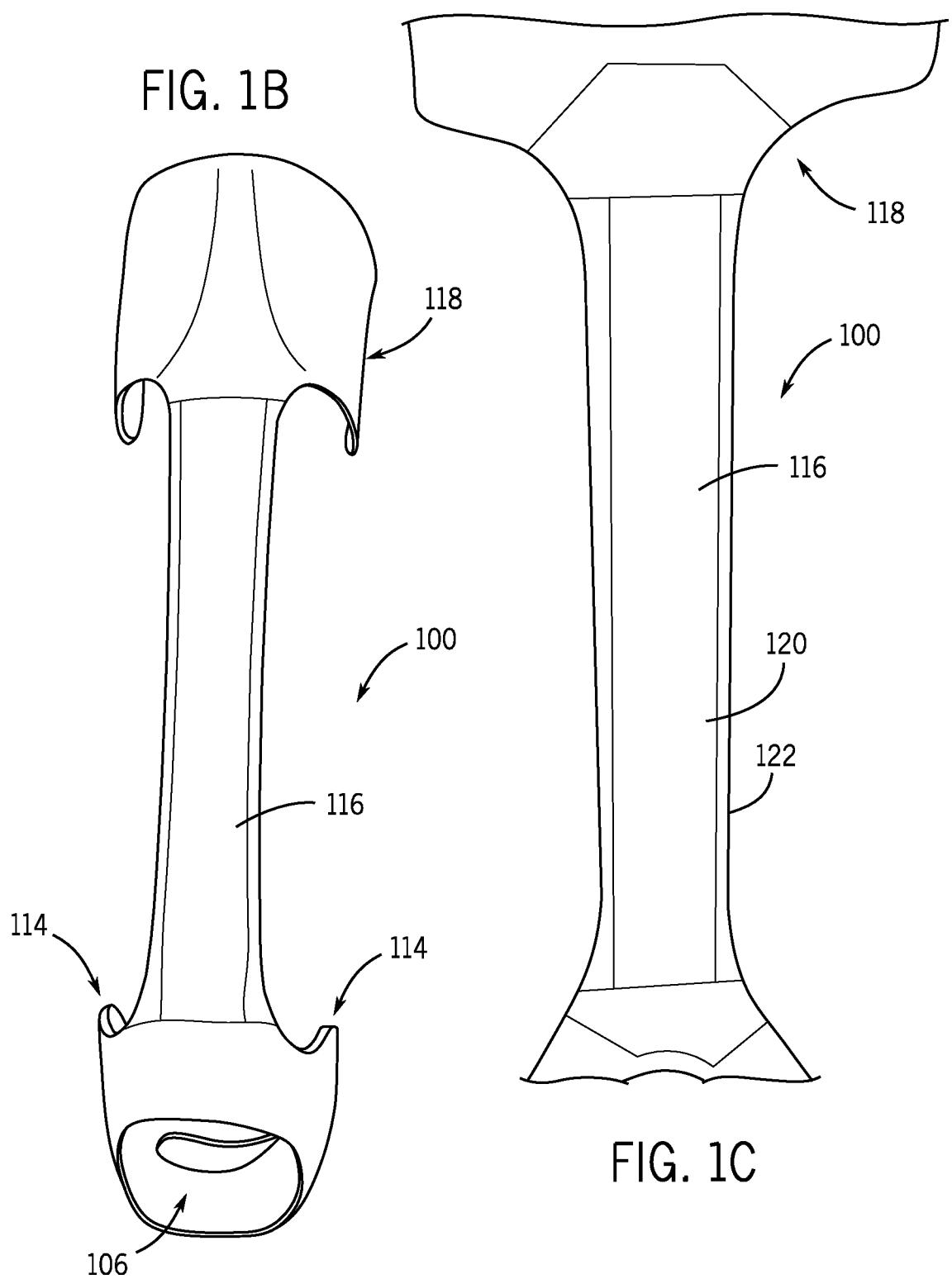

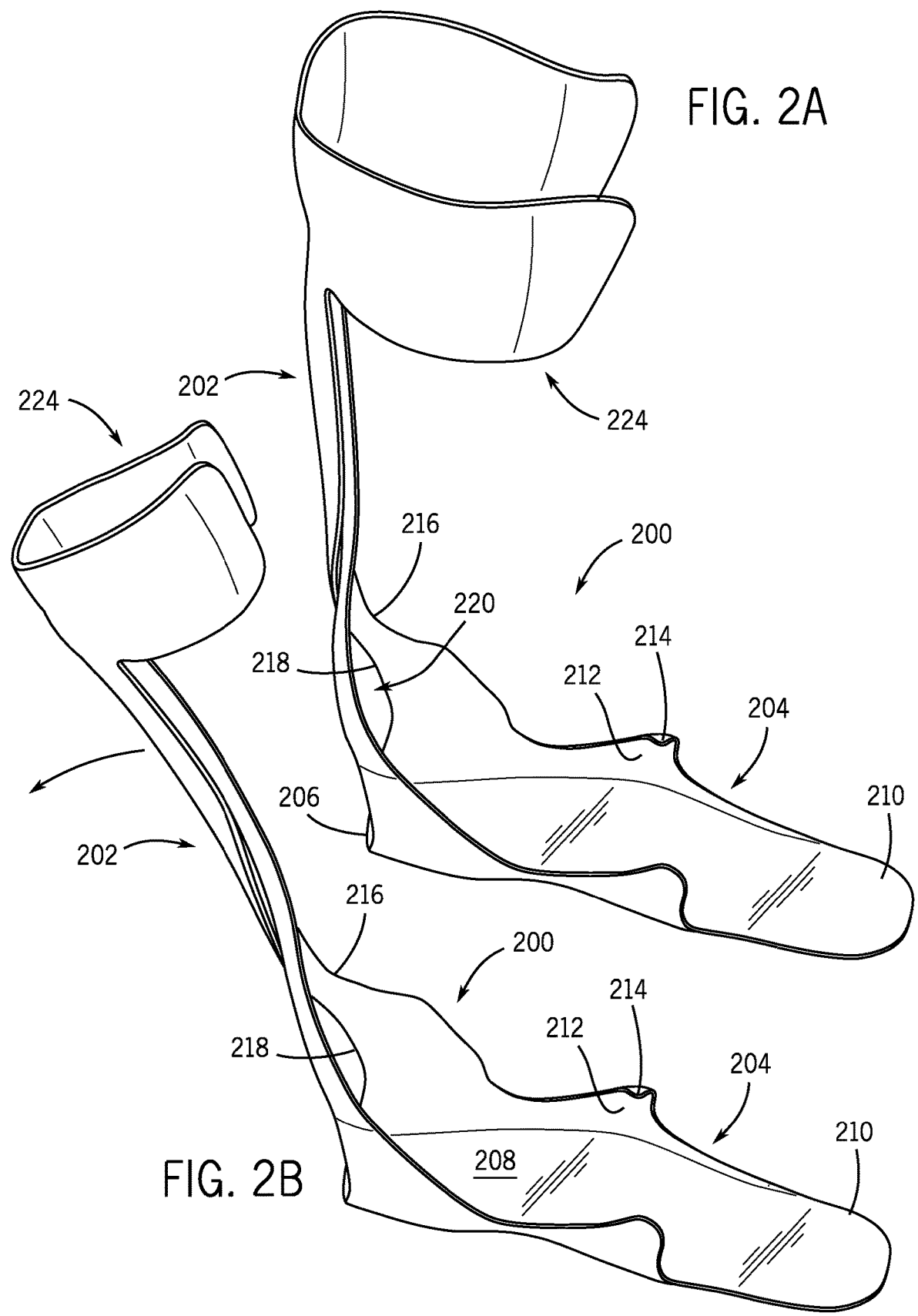

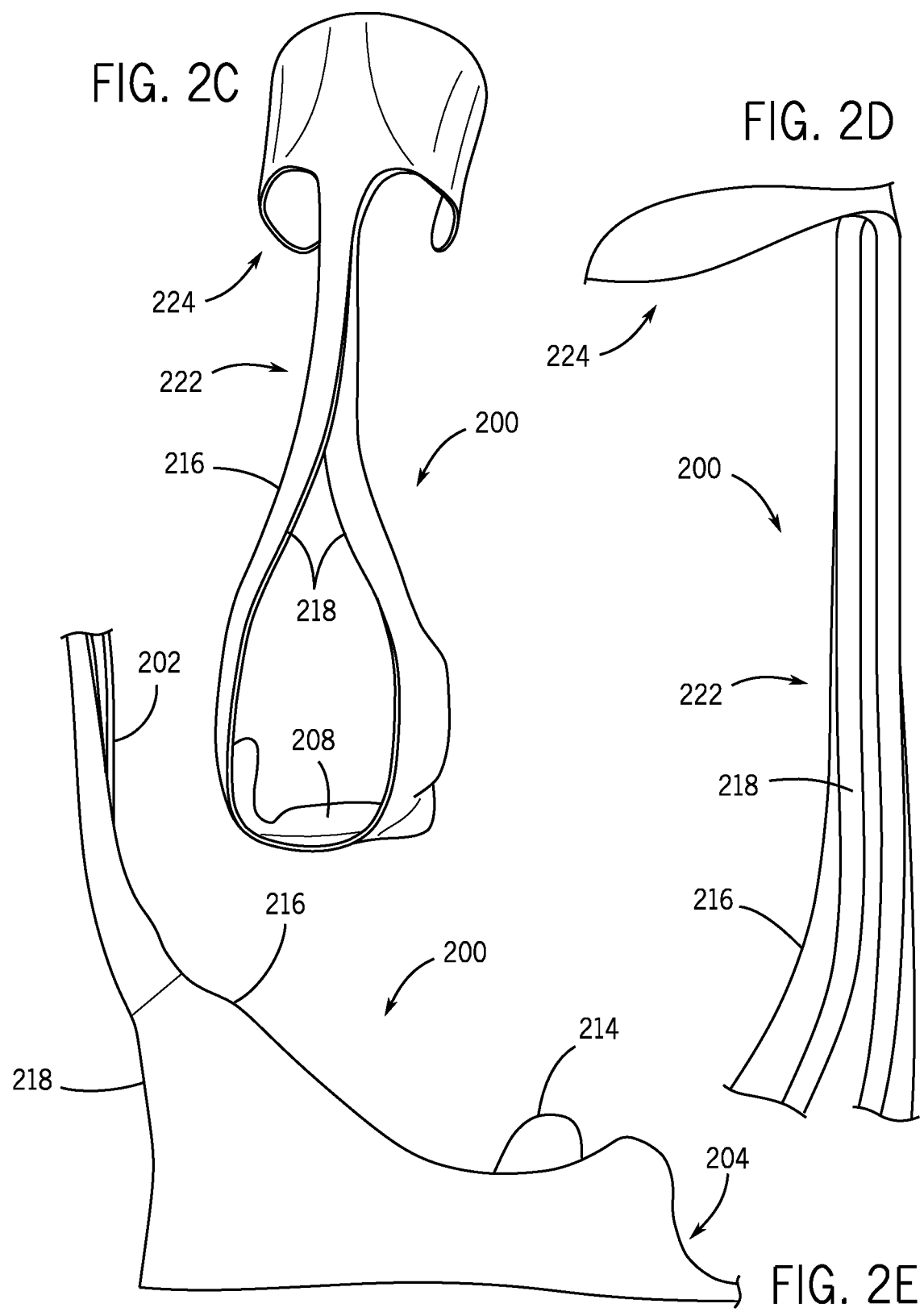

To begin the process of manufacturing a custom AFO, a patient's leg, ankle, and foot are cast [Block 400].

The cast is then removed from the patient's leg [Block 410].

The cast is sealed at the toe end of the cast and a plaster (e.g., Gypsum plaster) that has been mixed with water is poured into the cast [Block 420].

Once the plaster dries, the cast can be removed from the hardened plaster, which now represents a "positive mold" of the patient's leg, ankle, and foot [Block 430].

The plaster mold is then modified by adding material (e.g., plaster) to certain areas of the plaster mold to create a modified plaster mold [Block 440].

A thermoplastic that has been sufficiently heated so that it is pliable is wrapped around the modified plaster mold [Block 450].

Once the thermoplastic hardens around the modified plaster mold, the thermoplastic may be removed from the modified plaster cast [Block 460].

The inner brace shell can be cut to shape according to the illustration in FIG. 2 [Block 470].

The modified plaster mold is modified again by adding additional material (e.g., plaster) to the posterior side of the modified plaster mold to form a second modified plaster mold [Block 480].

Using the second modified plaster mold, a "dummy mold" is formed by molding a thermoplastic over the second modified mold and, then, removing the mold after it hardens [Block 490].

Layering sheets or layers of carbon fiber and/or fiberglass on the dummy mold in the areas that will ultimately form the outer brace once the carbon fiber and/or fiberglass hardens [Block 500].

A thin layer of thermoplastic is positioned over the strut member [Block 510].

A layer of plastic wrap, or similar material, is wrapped over the layers of carbon fiber and the thin layer of thermoplastic [Block 520].

The entire assembly including the dummy mold, carbon fiber, and the thin layer of thermoplastic may be sealed in a vacuum sealed bag [Block 530].

The next step is to put the dummy mold, carbon fiber, thin layer of thermoplastic, plastic wrap, and vacuum sealed bag in oven to bake [Block 540].

The carbon fiber and thin layer of thermoplastic can be removed from the dummy mold and plastic wrap [Block 550].

The edges of the thin thermoplastic can be trimmed and the carbon fiber on the calf-cuff member and the lower support member can be trimmed to the shape identified in FIG. 2A-2D [Block 560].

FIG. 4

After the inner brace shell is manufactured [Blocks 450-460], these steps are repeated a second time to form a second inner brace shell [Block 600].

Layers of carbon fiber are first laid up on the foot plate, sidewall areas, and calf-cuff of the second inner brace shell [Block 610].

Epoxy resin is added to strips of fiberglass and the strips of fiberglass are laid on the second inner brace shell with the respective ends of the strips protruding into each of the calf-cuff member and the lower support member [Block 620].

A thin layer of plastic wrap, or similar material, is wrapped over the assembly [Block 630].

The entire assembly including the second inner brace shell, carbon fiber, fiberglass and the plastic wrap may be sealed in a vacuum sealed bag [Block 640].

Put the entire assembly, including the vacuum sealed bag, in oven to bake [Block 650].

After baking in the oven for a sufficient time to harden the material, the carbon fiber and fiberglass can be separated from the second inner brace shell and plastic wrap [Block 660].

Portions of the strut members, the calf-cuff member, and the lower support member may be trimmed to the shape identified in FIG. 1 [Block 670].

FIG. 5

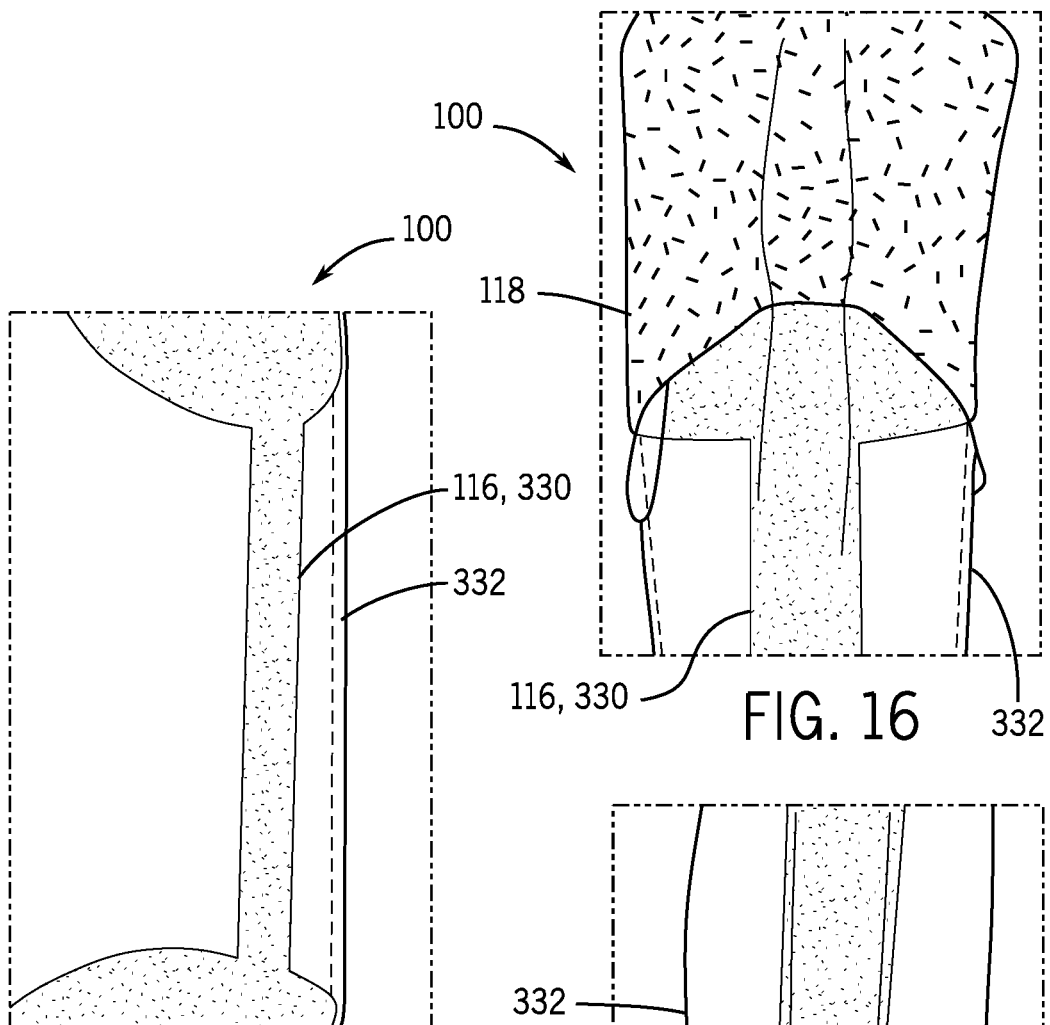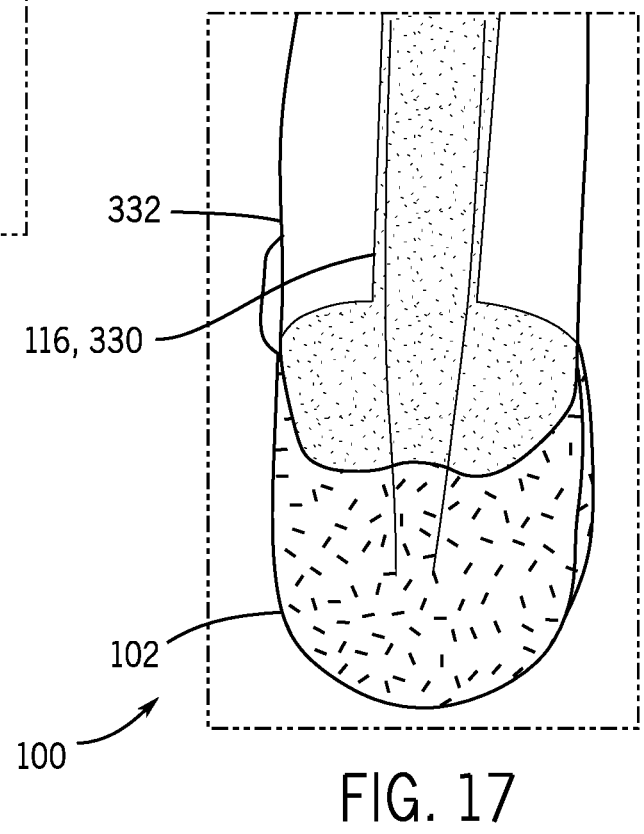

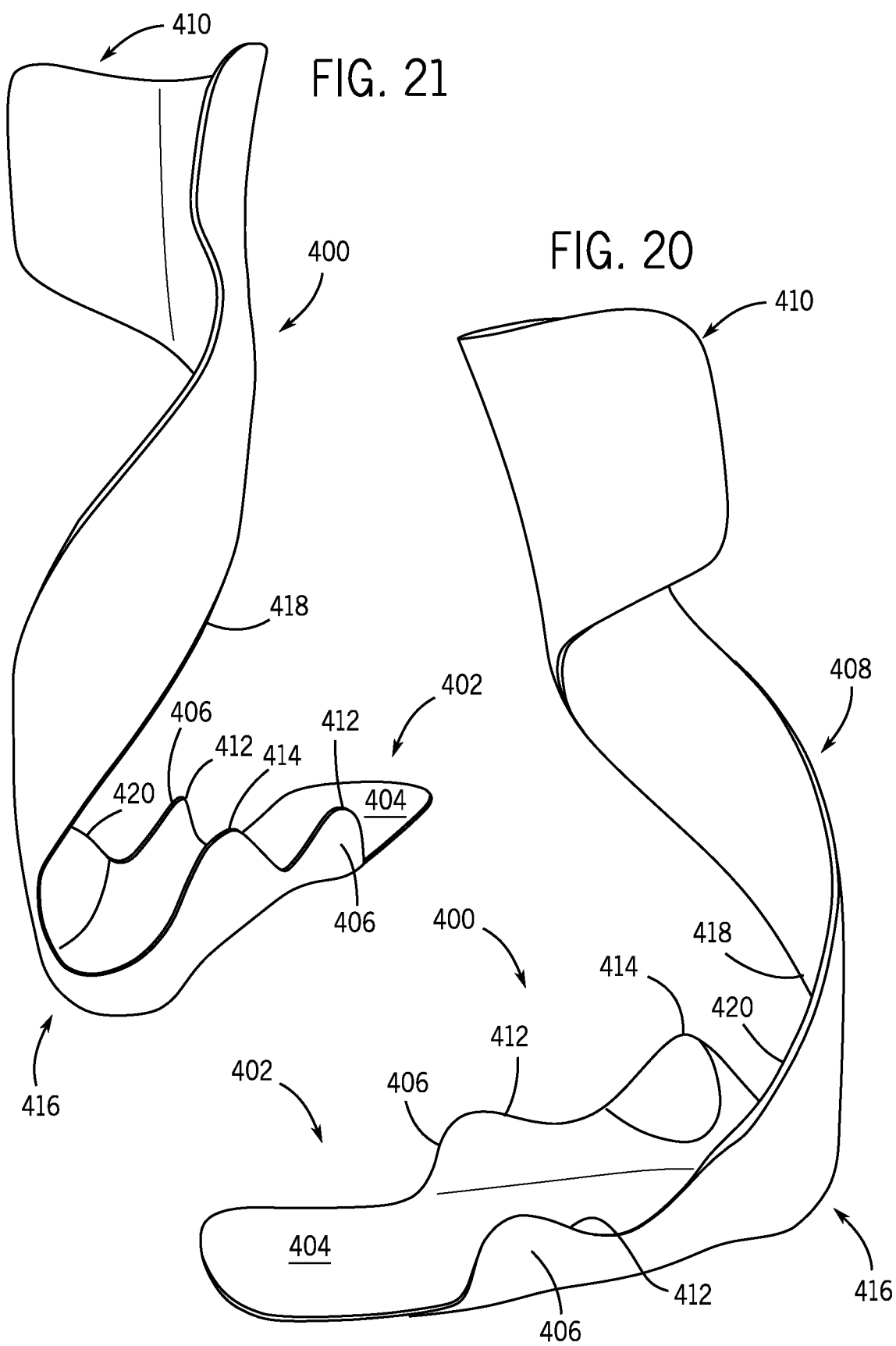

ANKLE-FOOT ORTHOSIS AND METHOD OF MANUFACTURE

CROSS-REFERENCE TO RELATED APPLICATIONS

The present application is a continuation-in-part ("CIP") application of, and claims priority to, U.S. patent application Ser. No. 14/859,025, which was filed Sep. 18, 2015, entitled "ANKLE-FOOT ORTHOSIS AND METHOD OF MANUFACTURE," and is hereby incorporated by reference in its entirety into the present application.

U.S. patent application Ser. No. 14/859,025 claims priority under 35 U.S.C. § 119 to U.S. Provisional Patent Application No. 62/052,615, which was filed Sep. 19, 2014, entitled "ANKLE-FOOT ORTHOSIS AND METHOD OF MANUFACTURE," and is hereby incorporated by reference in its entirety into the present application.

TECHNICAL FIELD

Aspects of the present disclosure involve orthoses, and more particularly, involve ankle-foot orthoses.

BACKGROUND

A variety of medical conditions may cause a patient to use an orthosis, which is a device that is externally applied to a patient's body to aid or supplement the patient's neuromuscular and skeletal system. Patients with hypotonia, for example, may have low muscle tone in certain leg muscles and may require the aid of an orthosis to provide support to lesser toned muscles. The orthosis helps the patient walk without collapsing forward or hyperextending backwards due to the inability of the lesser toned muscles to support the patient's body. As another example, patients with hypertonia may have high muscle tone in certain leg muscles (e.g., calf muscle) and may require the aid in an orthosis to position the foot in a relaxed or more natural position, and to help the make sure the foot does not hang and drag as the patient walks. With these types of conditions, among others, an ankle-foot orthosis (hereinafter "AFO") may be beneficial to help correct the imbalance of muscles in the patient's legs.

An AFO is a type of orthosis that supports both the foot and the ankle by controlling the position and motion of the ankle. As mentioned above, an AFO can be used for both weak, lesser toned limbs and contracted limbs. In addition, an AFO can be used for immobilization purposes (e.g., broken bone). Conventional AFO's form an "L" shape with an upper support that contacts a posterior side of a patient's lower leg with a strap securing around the patient's calf and a lower support that contacts an inferior side of the patient's foot. In conventional AFO's, there may or may not be a hinge mechanism at the ankle and there may or may not be additional straps throughout the "L" shape to secure the brace to the patient's leg.

Certain AFO designs may also include a Supra-Malleolar orthosis (hereinafter "SMO") that fits within the AFO to provide additional forefoot, mid-foot, and subtalar stability. Conventional SMO's wrap around a patient's foot and ankle to compress the soft tissue of the foot. The compression of the SMO helps to stabilize the foot and ankle, which helps the patient develop a more natural gait when walking.

While beneficial and useful to patients, some conventional AFO designs still suffer from many drawbacks.

SUMMARY

Aspects of the present disclosure may involve an ankle-foot orthosis for a lower leg including a calf, ankle, and foot of a patient. The ankle-foot orthosis may include a foot plate, a calf-cuff member, and a support member. The foot plate may include a toe side, a heel side opposite the toe side, a medial side including an arch region, and a lateral side opposite the medial side. The calf-cuff member may be configured to abut the calf of the patient. The support member may extend between the foot plate and the calf-cuff member, the support member consisting of a strut member including a curved lower section and a straight upper section, the curved lower section extending from the arch region of the medial side of the foot plate to a posterior position above the heel side of the foot plate, the curved lower section transitioning to the straight upper section at the posterior position, the straight upper section extending superiorly to the calf-cuff member.

In certain instances, the heel side defines a gap between the strut member and the foot plate.

In certain instances, the heel side of the foot plate may be unconnected to the strut member.

In certain instances, the strut member may be widest at the arch region.

In certain instances, the foot plate may be custom contoured to the foot of the patient.

In certain instances, the calf-cuff may be custom contoured to the calf of the patient. In certain instances, at least one of the foot plate or the calf-cuff member may be custom contoured to the calf of the patient, and an inner surface of the strut member may be not custom contoured to the patient.

In certain instances, a heel portion of an inner brace positioned within the ankle-foot orthosis extends further posteriorly than any portion of the ankle-foot orthosis.

In certain instances, the strut member may be constructed of carbon fiber.

In certain instances, the strut member may be constructed of layers of bi-directional and uni-directional carbon fiber.

Aspects of the present disclosure may involve a method of manufacturing a custom ankle-foot orthosis for a patient's lower leg and foot, the method may include: forming an inner brace from molding a first material over a first portion of a positive mold of the patient's lower leg and foot; modifying the positive mold to form a modified positive mold; and forming an outer brace by molding at least one second material over a second portion of the modified positive mold.

In certain instances, the first material may be a thermoplastic material.

In certain instances, the at least one second material may include carbon fiber.

In certain instances, the at least one second material further may include a thermoplastic material.

In certain instances, the positive mold may include a cast of the patient's lower leg and foot.

In certain instances, modifying the positive mold to form the modified positive mold may include removing custom contouring aspects of the positive mold.

In certain instances, modifying the positive mold to form the modified positive mold may include forming a flattened portion of the positive mold.

In certain instances, the flattened portion of the positive mold may include a band extending from a posterior region to a medial arch region.

In certain instances, the outer brace may include a foot plate, a calf-cuff member, and a strut member coupled between the foot plate and the calf-cuff member, the flattened portion of the positive mold may include an area to which the strut member may be molded.

In certain instances, the outer brace may include only one strut member including the strut member.

BRIEF DESCRIPTION OF THE DRAWINGS

Example embodiments are illustrated in referenced figures of the drawings. It is intended that the embodiments and figures disclosed herein are to be considered illustrative rather than limiting.

FIG. 1B is a back view of the first embodiment of the outer brace of FIG. 1A;

FIG. 1C is a close-up front view of the first embodiment of the outer brace of FIG. 1A;

FIG. 2A is a perspective view of a second embodiment of an outer brace of an AFO;

FIG. 2B is a perspective view of the outer brace of FIG. 2A flexing in a simulated plantarflexion position of a patient's leg;

FIG. 2C is a back view of the outer brace of FIG. 2A;

FIG. 2D is a close-up side view of overlapping struts in the outer brace of FIG. 2A;

FIG. 2E is a side view of the outer brace of FIG. 2A;

FIG. 4 is a flowchart of the manufacturing process for an embodiment of the AFO;

FIG. 5 is a flowchart of the manufacturing process for another embodiment of the AFO;

FIGS. 15-17 are views of the outer brace before trimming excess thermoplastic from around the strut member;

FIG. 20 is a front perspective view of a third embodiment of an outer brace of an AFO;

FIG. 21 is a back perspective view of the third embodiment of the outer brace of FIG. 20;

DETAILED DESCRIPTION

Aspects of the present disclosure involve an AFO that combines energy returning and flexible characteristics of carbon fiber with enhanced flexibility traits of thermoplastics, among other features, to provide an AFO that helps a patient develop a more natural gait across a range of motion from walking to running. More particularly, in one example, an AFO with a strut formed of the combined materials provides for a more robust AFO that can withstand bending stresses placed on the AFO and particularly the strut by active patients. Aspects of the present disclosure also involve an AFO that includes a multi-strut configuration that provides sufficient flexibility and energy return, while at the same time providing enhanced robustness that can withstand active bending, whether intentionally or unintentionally from patients.

In the various possible implementations discussed herein, the AFO includes an outer brace and an inner brace. The inner brace is a form-fitted brace that is customized to match the contours of a patient's foot and ankle. The inner brace is semi-rigid and formed from a thermoplastic or similar material. The inner brace securely attaches to the patient's foot/ankle and fits within the outer brace. The outer brace includes a foot plate, a calf-cuff, and either a single strut member or a pair of strut members that couples the foot plate to the calf-cuff. The foot plate and the calf-cuff of the outer brace may include a custom-fit contour of the patient's specific anatomy, while the strut members may be formed to provide a consistent and predictable flexion point that is near or below the ankle regardless of the patient's specific anatomy. The outer brace may be formed from layer of carbon fiber, fiberglass, and/or thermoplastic to provide the necessary resistance to support the patient's leg in a natural position. Overall, the foot plate and the calf-cuff secure the AFO to the patient's foot and lower leg, while the strut is the active component that flexes and provides support to the patient's ankle and foot as they stand, walk, run, and otherwise go about their daily routine.

Figure 1A:
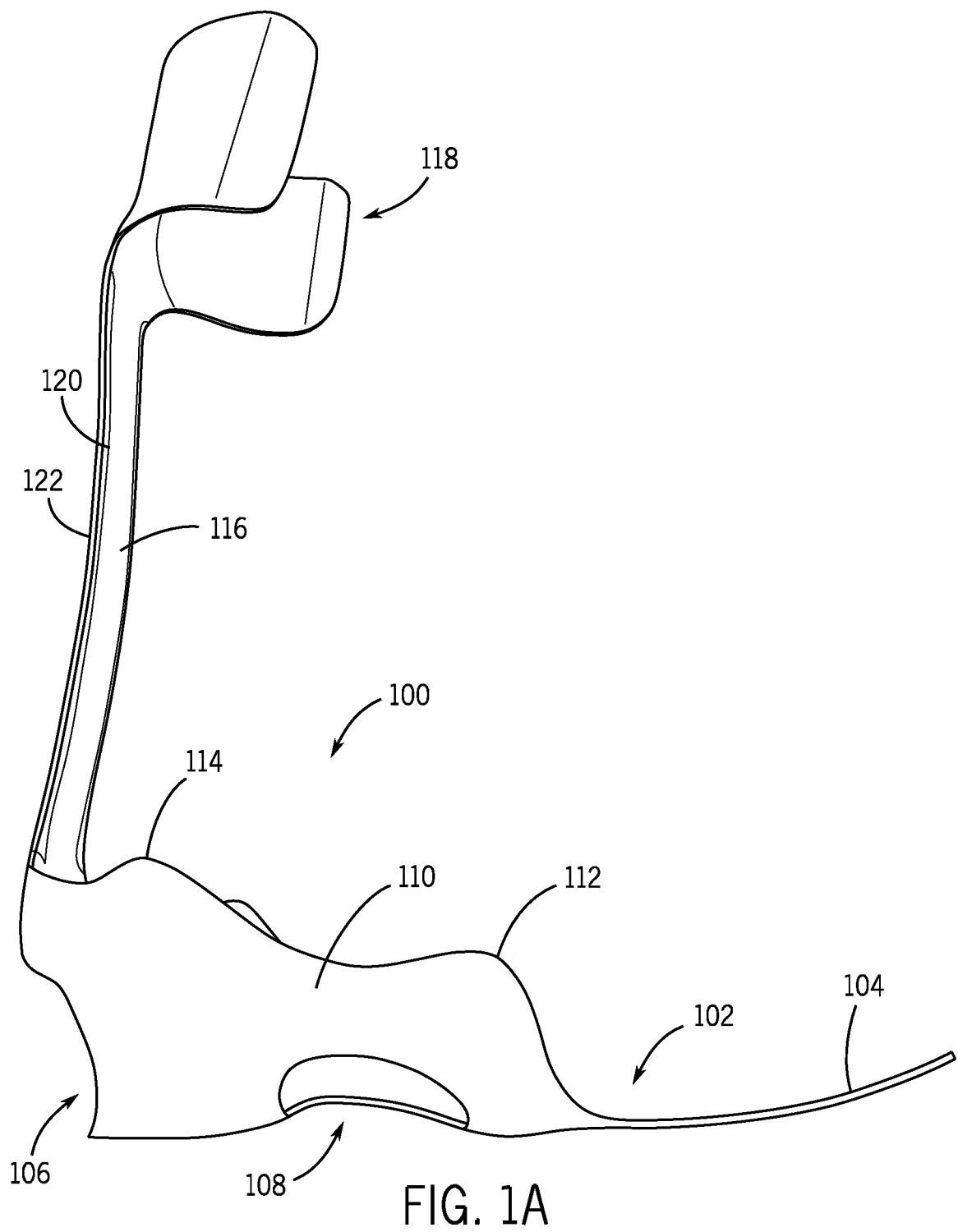
FIG. 1A is a side view of a first embodiment of an outer brace of an AFO.

Referring to FIGS. 1A-1C, an outer brace 100 is shown in a side view, rear view, and front view, respectively. The outer brace 100 includes a lower support member 102 that partially wraps around the foot and ankle of a patient's leg. In particular, the lower support member 102 wraps around portions of the ankle area and the plantar surface of the foot or inner brace while leaving the dorsal area of the foot or inner brace open. The lower support member 102 includes a foot plate 104 that contacts an inferior surface of the inner brace (shown in FIG. 3) and runs from a heel-end of the outer brace to a toe-end of the outer brace. As seen in FIG. 1, the foot plate 104 may include open areas to reduce weight or to provide movement for the inner brace, which is not shown in FIG. 1. In particular, the foot plate 104 may include an open area 106 in the area of the calcaneus, or heel bone, and may also include an inferior open area 108 in the mid-foot region. The foot plate couples to or transitions to a pair of sidewall members 110 on either side of the outer brace 100. Each of the sidewall members 110 includes a mid-foot raised edge 112 that wraps around a mid-portion of the patient's foot/inner brace. Moving distally from the mid-foot raised edge 112 at the mid-portion of the outer brace 100, the mid-foot raised edges 112 taper down to the foot plate 104 at the toe-end of the outer brace 100. Moving proximally from the mid-foot raised edge 112, each of the mid-foot raised edges 112 dips towards the foot plate 104 and then transitions upward again to a hind-foot raised edge 114. Again, moving proximally from the hind-foot raised edges 114, each of the hind-foot raised edges 114 dips towards the foot plate 104 and then couples with a strut member 116 at a proximal-most end of the heel-end portion of the outer brace 100.

The strut member 116 extends from the lower support member 102 on a posterior side of the foot above the calcaneus to a calf-cuff member 118. The strut member 116 is a flexible/resilient semi-rigid member formed from layers of carbon fiber 120 and one or more layers of thermoplastic 122 or similar material. The strut member 116 extends on a posterior side of a patients calf and provides resistance and support between the lower support member 102 and the calf-cuff member 118. While the lower support member 102 and the calf-cuff member 118 are contoured to the patient's particular anatomy, the strut member 116 is substantially flat or straight in a medial-lateral direction, in one implementation. Such a flat cross-section allows for maximum strength when a patient's foot is in dorsiflexion as well as plantarflexion. Aspects of this disclosure involve a strut member formed of a combination of carbon fiber 120 and thermoplastic 122. Aspects of the disclosure also contemplate a substantially flat strut member 116, as compared to a contoured strut matching the ankle above a patients heel. Aspects of the present disclosure also contemplate a strut member 116 with combined materials as well as a substantially flat portion above the heel It has been found that while functional and reliable, introducing variables associated with the strut member 116 could affect the flexion point of the AFO. For example, a strut member 116 that is contoured to the patient's leg may introduce areas of stress concentrations, such as abrupt directional changes along the extension of the strut member 116 between the lower support member 104 and the calf-cuff member 118. In some instances, it may be preferable to include a contoured strut where enhanced rigidity is sought without adding additional carbon layers. The stress concentrations, however, may cause the strut member 116 to bend at the stress concentrations as opposed to bending at the point of connection with the lower support member. Also, the stress concentrations may be subject to increase and/or abnormal wear, which may lead to failure of the AFO. Accordingly, in one possible implementation, the strut member 116 is flattened between the lower support member 104 and the calf-cuff member 118 such that the strut member 116 may have more consistent mechanical properties that are not dependent on the specific contouring of the posterior surface of the patient's leg.

Referring to the calf-cuff member 118, it may be manufactured from carbon fiber 120 and may wrap partially or wholly around the calf of the patient. As with the lower support member 104, the calf-cuff member 118 may be contoured specifically to the patient's calf. The calf-cuff member 118 may additionally include a strap (not shown), such as a VELCRO® strap, that wraps around the front of the patient's leg and secures the patient's leg to the calf-cuff member 118. With respect to the calf-cuff member 118 and the lower support member 104, while described as being formed of carbon fiber 120, which allows the AFO to be a unified piece, it is possible to fabricate the calf-cuff and lower support member from other materials and couple the strut member 116 therebetween.

In use, the AFO functions as follows. A patient positions their foot within an inner brace and secures the foot accordingly. The patient then secures an outer brace 100 to the foot with the inner brace already secured. In this step, the patient may secure the calf-cuff member 118 to the calf area by cinching a strap around the calf, or otherwise. As seen in FIG. 1A, the outer brace 100 is positioned in a neutral position (i.e., with a patient's foot in neither dorsiflexion nor plantarflexion) or in slight dorsiflexion or plantarflexion as needed for the specific patient. As such, once the outer brace 100 is secured to the patient's leg and the patient begins walking, the outer brace will flex about the strut member 116 at the point of attachment to the lower support member 104, and for a distance above the point of attachment. Thus, the strut member 116 will flex to some degree along its length depending on the activity of the patient. For example, as the patient steps forward with one leg while putting weight on the leg with the AFO, the AFO will flex in dorsiflexion to allow adequate step length and provide resistance to the patient's leg from collapsing forward. As the stance leg moves into terminal stance position it uses energy stored from dorsiflexed position and releases energy to assist with active plantarflexion during push-off. This motion allows more normal and efficient walking pattern and also allows for active muscle use by the patient and, therefore, strengthening of those muscles. And, as the patient steps forward with the leg with the AFO, the AFO will flex in plantarflexion as the heel area contacts the floor and transfers weight onto the leg with the AFO (loading response). The strut will flex to a greater extent if the patient is running or jumping as opposed to walking, for example.

Reference is now made to FIGS. 2A-D, which are views of a second embodiment of an outer brace 200 of an AFO that employs multiple struts or strut members 202 (in this example, two struts). Referring to FIG. 2A, the outer brace 200 includes a lower support member 204 that is somewhat similar to the first embodiment illustrated in FIG. 1, but with modifications to the heel-end portion 206 of the lower support member 204 in order to change the stress concentrations and support the two struts 202 with a unified lower support and strut. As with the first embodiment, the second embodiment of the lower support member 204 partially wraps around the ankle area and the plantar area of the foot or inner brace while leaving the dorsal area of the foot or inner brace open. The lower support member 204 includes a foot plate 208 that contacts the inferior surface of the inner brace and runs from the heel-end 206 of the outer brace to a toe-end 210 of the outer brace 200. The foot plate 208 couples to or transitions to a pair of sidewall members 212 on either side of the outer brace. Each of the sidewall members 212 includes a fin-shaped edge 214 that wrap around a mid-portion of the patient's foot/inner brace. Moving distally from the fin-shaped edge at the mid-portion of the outer brace 200, the fin-shaped edges 214 taper down to the foot plate 208 at the toe-end 210 of the outer brace 200. Moving proximally from the fin-shaped edge 214 at the mid-portion of the outer brace 200, each of the fin-shaped edges 214 dips towards the foot plate 208 and then transitions upward at an approximate 45 degree angle where it forms an anterior side edge 216 of a strut member 202 that extends towards the calf of the patient. A posterior side edge 218, opposite the anterior side edge 216, of the strut member 202 tapers down to the foot plate 208 while leaving open a posterior end of the heel-end 206 of the outer brace 200. Stated differently, the foot plate 208 terminates at the heel-end 206 of the outer brace 200 and the sidewall members 212 do not wrap around the posterior end of the heel-end 206. The opening 220 formed by the pair of struts 202 is a large opening in the area of the calcaneus and allows for movement of the inner brace relative to the outer brace 200. Additionally, the opening 220 formed by the pair of struts 202 allows each strut to function independently so that the flex point comes from a point below the ankle axis. If the struts 202 were coupled together above the ankle, then the flex point would likely be above the ankle. The opening 220 formed by the pair of struts 202 allows for an additional range of motion since the flex point is below the ankle.

As mentioned above, the sidewall members 212 of the lower support member 204 couple to or transition to a pair of strut members 202, which extend upward towards the patient's calf. In the second embodiment of the outer brace 200 and still referring to FIGS. 2C-2D, each strut member 202 wraps around from the sidewall members 212 to a point 222 above the center heel-end 206 of the lower support member 204. At the centered convergence point 222, the struts 202 overlap for the extension from the center point 222 to the calf-cuff member 224. The struts 202 couple with the calf-cuff member 224 on a posterior side of the patient's calf. The calf-cuff member 224 is similar to as described in FIG. 1.

Regarding the flexion of the outer brace 200, each of the strut members 202 twists or rotates between 45 and 90 degrees from the point where the struts 202 extend from the sidewall members 212 and the center point 222 above the heel-end 206. Stated differently, the struts 202 form a substantially flat cross-section and initially extend upward from the outer brace 200 on opposites sides of the heel. The struts 202 then twist such that the flat area of each strut is parallel, overlapping, and roughly parallel to the tangent of the contour of the rear of the patient's leg at the point 222 where the struts 202 converge. As seen in FIG. 2B, when the outer brace 200 is in plantarflexion, the rotation of the strut members 202 provides a mechanism to facilitate flexion of the AFO. In particular, as the outer brace 200 is flexed in plantarflexion, the strut members 202 flex in a general region between the center point 222 and the sidewall members 212. Utilizing two strut members 202 in such a manner can increase the rigidity of the outer brace 200 and, thus, allow for less material in the heel area of the brace 200, as seen in FIG. 2C, which is a back view of the outer brace 200 of the second embodiment. Arranging the strut members 202 in this manner also allows the struts to independently flex according to the particular movements of the patient. The struts 202 may, for example, independently flex outward a small amount when the patient moves in dorsiflexion, which increases the strength of the struts 202 by reducing areas of stress concentrations.

Figure 3:
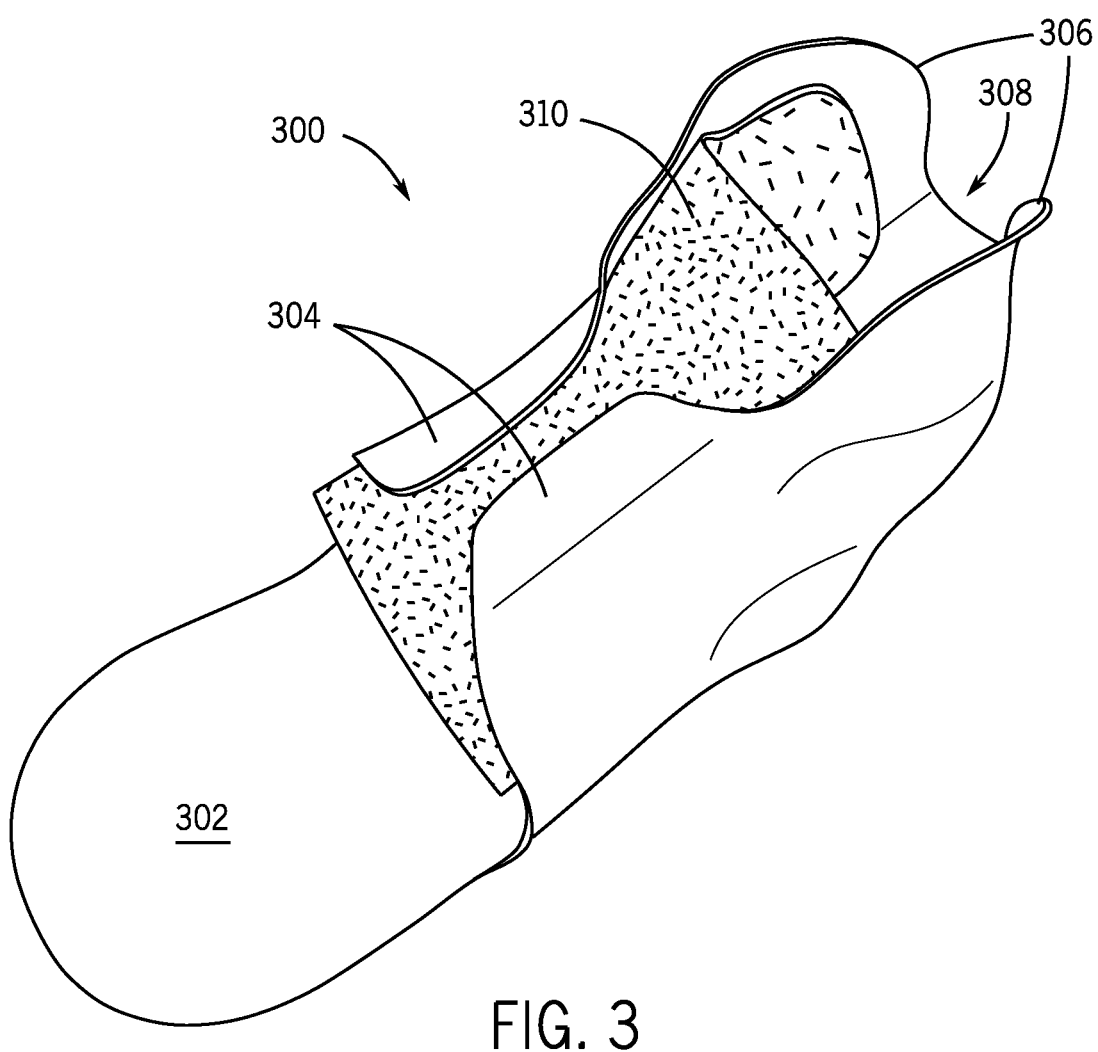
FIG. 3 is a perspective view of an inner brace of the AFO.

Referring now to FIG. 3, which is a perspective view of an inner brace 300 of the AFO, the inner brace 300 includes a plantar support member 302 that supports the inferior side of the patient's foot and side supporting members 304 that wrap around medial and lateral sides of the foot. Each of the side supporting members 304 includes a lip 306 at a top edge of the side supporting surface 304 to decrease painful rubbing of inner brace 300 with the upper ankle of the patient. Additionally, the inner brace 300 includes a recessed posterior portion 308 of the brace 300 where the two side supporting surfaces 304 meet posteriorly of the patient's calcaneus. The recessed posterior portion 308 allows for comfortable movement of the patient, in particular, during plantarflexion.

The inner brace 300 is form-fitted to a patient's foot and is securely attached to the patient's foot such that when the patient walks (i.e., with the inner brace positioned within the outer brace), the inner brace 300 moves with the patient's foot with little or no flex, while the outer brace 100, 200 may flex or move relative to the inner brace 300. The inner brace 300 may include a strap (not shown) and/or cushioning material on all or a portion of an inner surface of the inner brace. In particular, the cushioning material 310 may be positioned over boney portions of the foot or ankle to provide comfort to the patient when walking with the AFO.

As far as the construction of the AFO, the outer brace 200 may be manufactured entirely or partially from carbon fiber, which provides excellent flexibility and strength to weight ratios. In particular, the outer brace 200 may be manufactured from sheets or rolls of pre-impregnated carbon fiber (i.e., resin or epoxy is present in the carbon fiber weave) and "baked" in an oven in order to cure or harden the material. In certain embodiments, portions of the outer brace 200 may include fiberglass and resin materials. As an example, the strut members 202 may be fiberglass as opposed to carbon fiber. The inner brace 300, on the other hand, may be manufactured from a thermoplastic material, which is a polymer that becomes pliable or moldable above a specific temperature and returns to a solid state upon cooling. While the inner and outer brace 300, 200 are described as being constructed from the above materials, the braces may be manufactured from other materials as well.

The following discussion will focus on the manufacturing processes involved in making the outer and inner brace.

Figure 6:
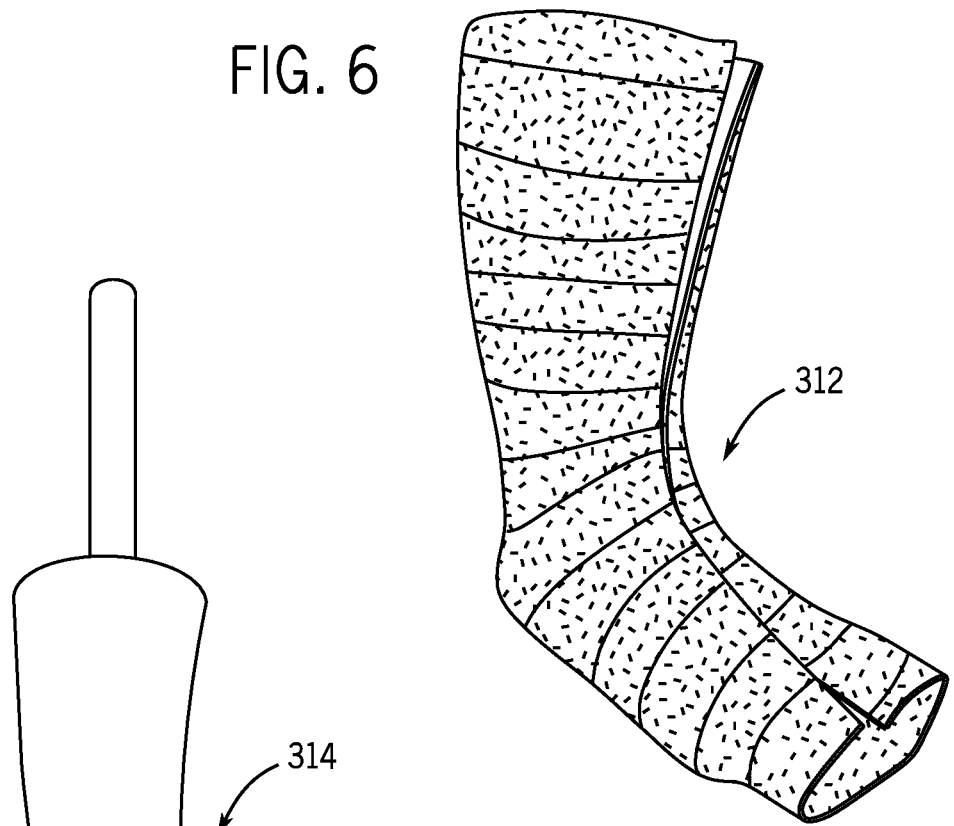
FIG. 6 is a perspective view of an empty cast.
Figure 7:
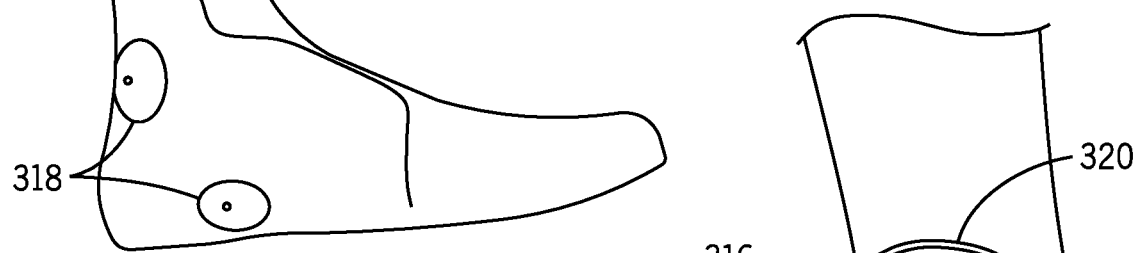
FIG. 7 is a perspective view of a positive mold formed from the empty cast.

To begin, reference can be made to FIGS. 4-5, which are flowcharts of the manufacturing process for the inner brace. First, the process of manufacturing a custom AFO involves casting a patient's leg, ankle, and foot [Block 400]. The casting may be done by putting a stockinet or sock on the patient's leg, ankle, and foot. Next, moistened, pre-impregnated fiberglass wrapping can be wrapped around the lower leg, ankle, and foot. Once the fiberglass cast hardens (e.g., 10 minutes), the cast may be cut along a superior side of the foot and along an anterior side of the leg such that the portion of the cast that contacts the inferior side of the foot and the posterior side of the leg remains intact and undamaged by the cutting. As seen in FIG. 6, the cast 312 is then removed from the patient's leg [Block 410]; the empty cast 312 represents a "negative mold" of the patient's leg, ankle, and foot. Next, the cast 312 is sealed at the toe end of the cast and a plaster (e.g., Gypsum plaster) that has been mixed with water is poured into the cast [Block 420]. As seen in FIG. 7, once the plaster dries, the cast 312 can be removed from the hardened plaster 314, which now represents a "positive mold" of the patient's leg, ankle, and foot [Block 430].

Figure 8:
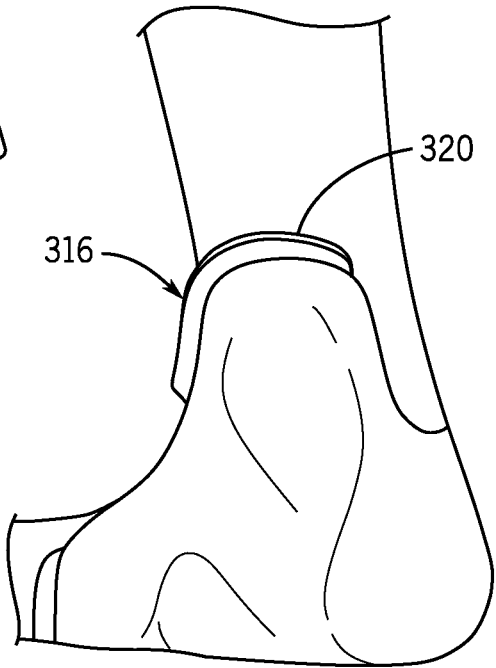
FIG. 8 is a close-up perspective view of a modification of the plaster mold.

The plaster mold 314 is then modified by adding material (e.g., plaster) to certain areas of the plaster mold 314 to create a modified plaster mold [Block 440] 316. For example, material 320 can be added to certain surfaces 318 that correspond to boney surfaces of the foot and ankle such as the ankle bones. The addition of material 320 to the plaster mold 314 means that any molds that are formed on or over the modified plaster mold 316 will provide more room for the patient's boney surfaces in the areas where the plaster was added to the plaster mold 314. In addition to adding material 320 to the surfaces 318 on the mold 314 that corresponds to the boney portions of the patient's leg, ankle, and foot, and as seen in FIG. 8, material 320 can be added to the plaster mold 314 in the area of the lip of the inner brace such that when a mold is molded to the modified plaster mold 316, the inner brace 300 will include the lip.

Figure 9:
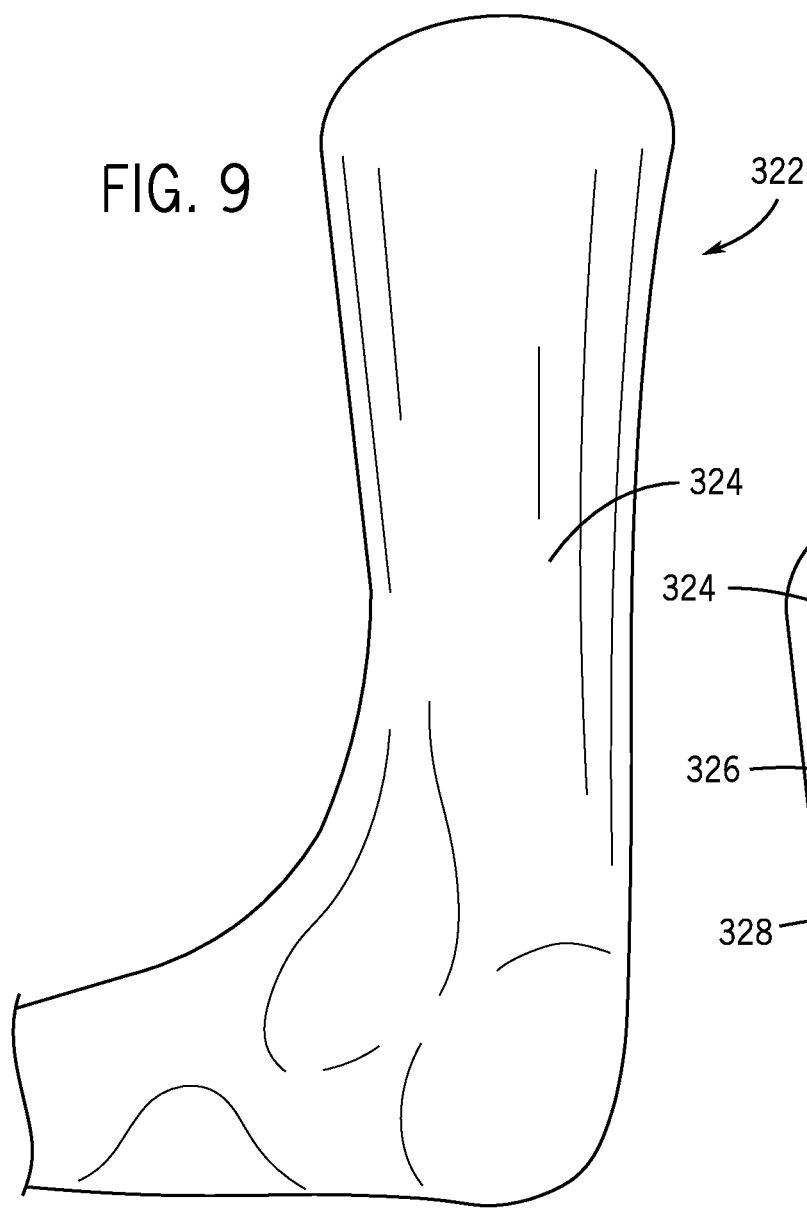
FIG. 9 is a rear isometric view of an inner brace shell.

The next step in the manufacturing process, as seen in FIG. 9, involves molding an inner brace shell 322. In this step, a thermoplastic 324 that has been sufficiently heated so that it is pliable is wrapped around the modified plaster mold 316 [Block 450]. In particular, the thermoplastic 324 can be wrapped around the modified plaster mold 316 from a single sheet of thermoplastic material and can be wrapped from a posterior side of the leg and an inferior side of the foot such that the thermoplastic meets or joins on a superior side of the foot and an anterior side of the leg. Once the thermoplastic 324 hardens around the modified plaster mold 316, the thermoplastic 324 may be removed from the modified plaster cast 316 [Block 460]. For example, the thermoplastic 324 may be cut along the superior side of the foot and the anterior side of the leg such that the sides of the brace 322 that correspond with the posterior side of the leg and inferior side of the foot remains intact.

Once the inner brace shell 322 is removed from the modified plaster cast 316, the inner brace shell 322 can be cut to shape according to the illustration in FIG. 2 [Block 470]. The inner brace shell 322 can be cut with a knife or shears, among other methods.

At this point, the process may diverge based on the particular embodiment of the outer brace is produced. For manufacturing the first embodiment of the outer brace 100, reference is made to FIGS. 4, 6-17 and [Blocks 480-560]. For manufacturing the second embodiment of the outer brace 200, reference is made to FIGS. 5-9, 18-19 and [Blocks 600-670].

The next step involves an additional modification of the modified plaster mold 316. The modified plaster mold 316 is modified again by adding additional material (e.g., plaster) to the posterior side of the modified plaster mold 316 to form a second modified plaster mold [Block 480]. In particular, the portion of the modified plaster mold that corresponds to about ¾ inch above the apex of the calcaneus is flattened. And, the flattening may extend to the calf. The flattening involves adding material medial-laterally M/L across the modified plaster mold 316, of FIG. 8 for example, so that a nearly flat surface extends up to the calf from the apex of the calcaneus. As will be discussed in further detail below, the flattening of this area facilitates forming a flat strut member that extends from the lower support member to the calf-cuff member. Forming a flat strut member, as opposed to a patient specific contouring strut member, may ensure uniform mechanical characteristics of the strut member. Otherwise, a strut member that is contoured to the patient's anatomy could exhibit stress concentrations that affect performance of the AFO. Additionally, such a strut member could affect the rehabilitation of the patient by altering the flexion point of the AFO.

Figure 10:
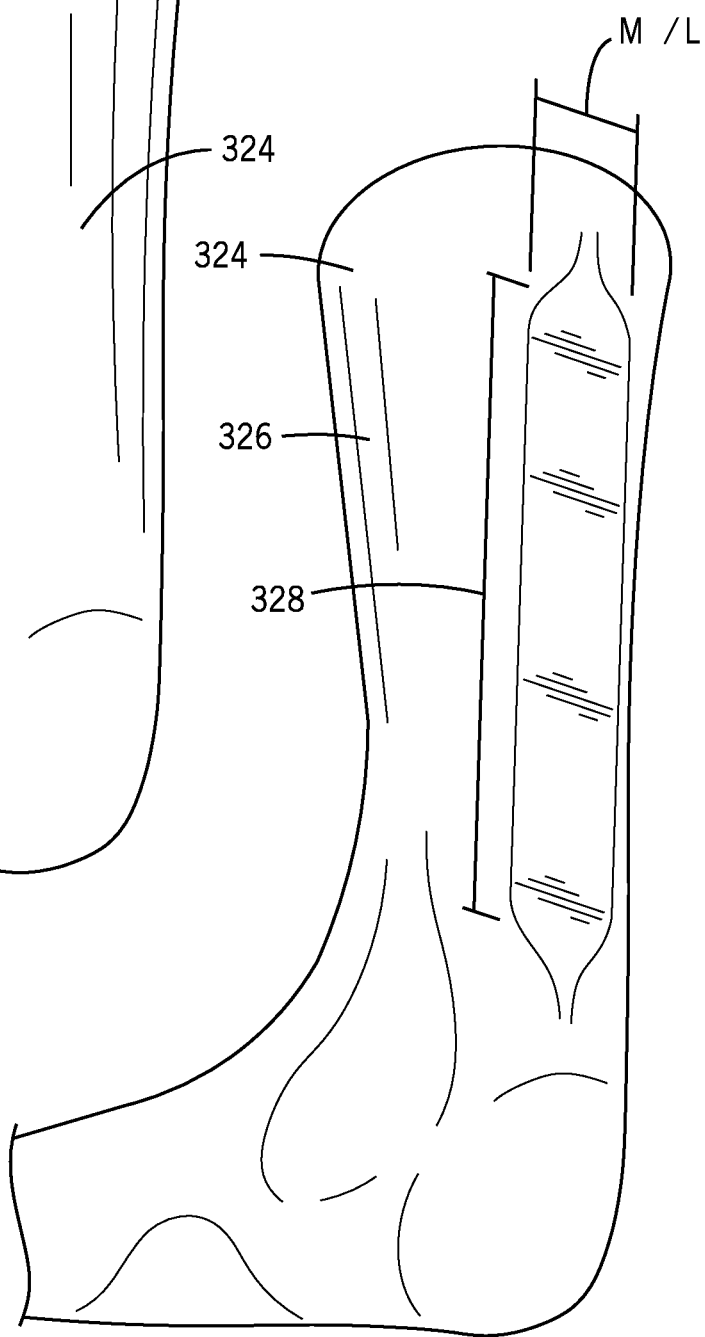
FIG. 10 is a rear isometric view of a dummy mold showing a flattened area on a posterior side of the mold.

Using the second modified plaster mold, a "dummy mold" 326 is formed by molding a thermoplastic 324 over the second modified mold and, then, removing the mold 326 after it hardens [Block 490]. As illustrated in FIG. 10, the posterior side of the dummy mold is flat 328 from just above the heel area to the calf area. The procedure is similar to as described with respect to molding the inner brace [Block 450], except that the dummy mold 326 is formed over the second modified plaster mold. Once the thermoplastic cools and hardens, the dummy mold 326 can be removed from the second modified plaster mold in the manner described with respect to the inner brace 300 removal [Block 460]. The dummy mold 326 provides a shell for "laying-up" or wrapping of layers of material that will ultimately become the outer brace 100. And, since the posterior side of the dummy mold 326 is flattened, the layers of material that are positioned on this area of the mold 326 will also be flat.

The next step involves layering sheets or layers of carbon fiber and/or fiberglass 330 on the dummy mold 326 in the areas that will ultimately form the outer brace 100 once the carbon fiber and/or fiberglass 330 hardens [Block 500]. Thus, when the carbon fiber and/or fiberglass 330 hardens, it will have an inner shape that corresponds to the outer shape of the dummy mold 326. And, since the dummy mold 326 includes a flattened surface 328 on a posterior side of the lower leg area of the dummy mold 326, when the carbon fiber and/or fiberglass 330 is layered on this area to form the strut member 116, the carbon fiber and/or fiberglass 330 will lay flat, which increases the strength of the strut member 116. Additionally, layering the carbon fiber or fiberglass 330 in such an orientation provides consistency that would not be achieved if the carbon fiber and/or fiberglass 330 was laid on a mold 326 that was contoured to the specifics of the patient's anatomy. As stated previously, having a flat strut member 116 reduces the possibility of stress concentrations, which could lead to pre-mature failure of the AFO. Thus, layering the carbon fiber or fiberglass 330 in a flat orientation leads to consistent manufacturing with less chance of failure.

Figure 11:
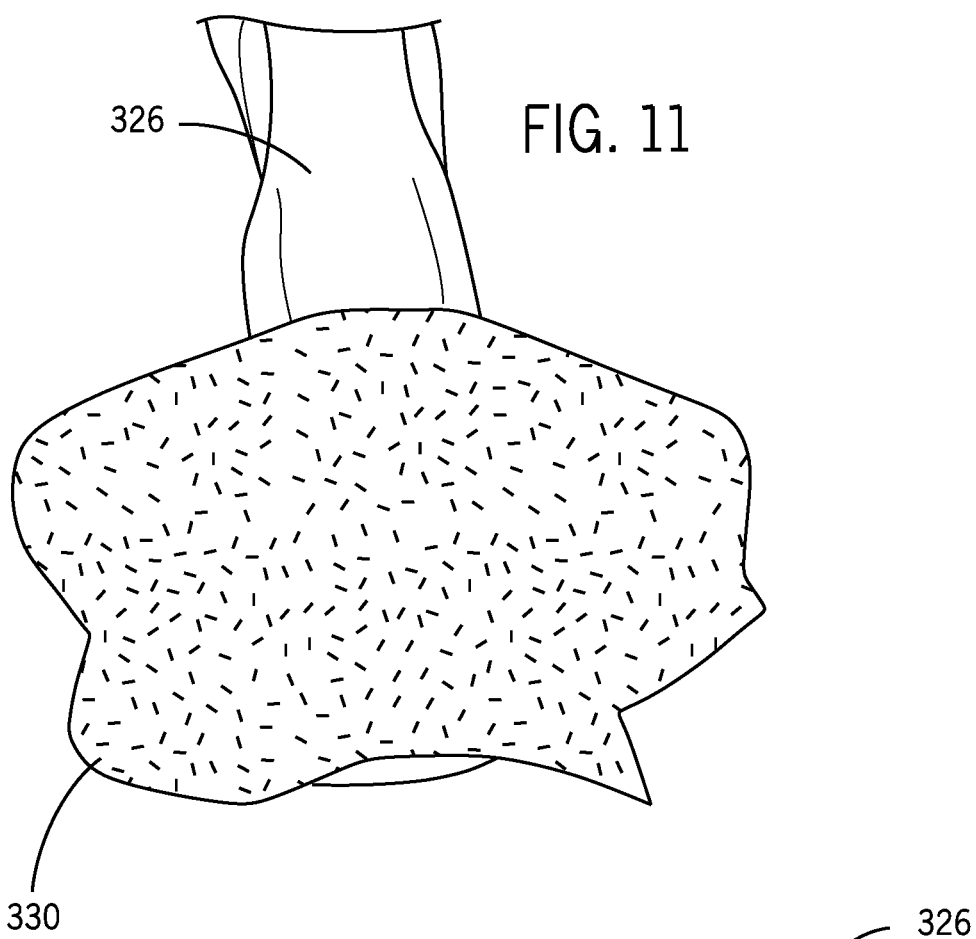
FIGS. 11-13 are views of the dummy mold with a first layer of carbon fiber being wrapped around the dummy mold.
Figure 12:
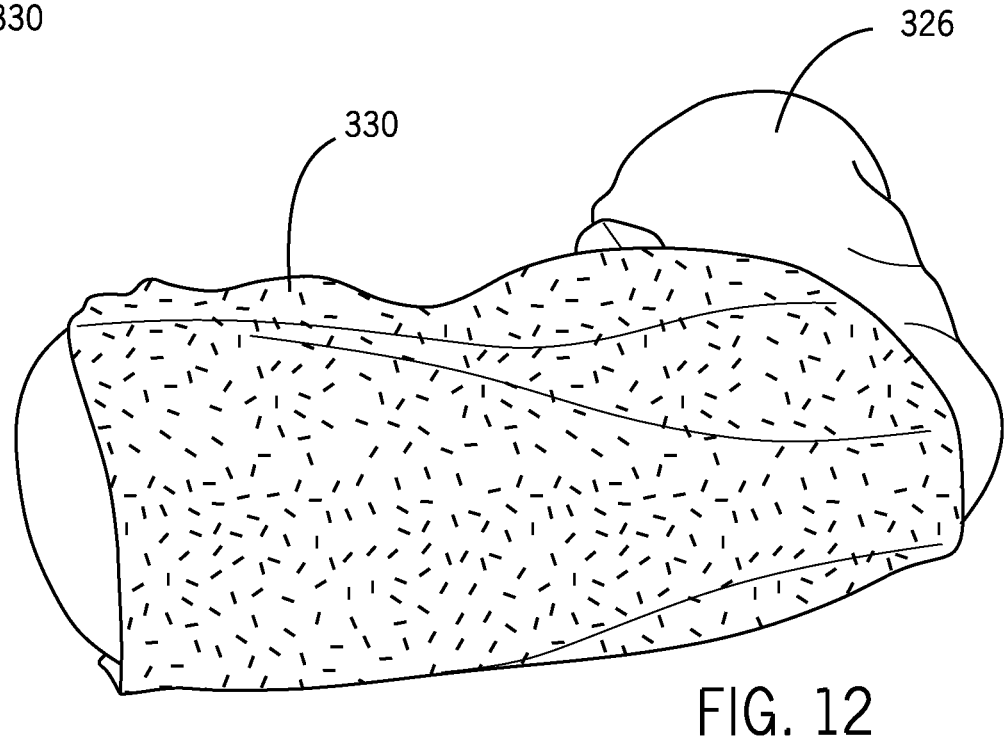
Figure 13:
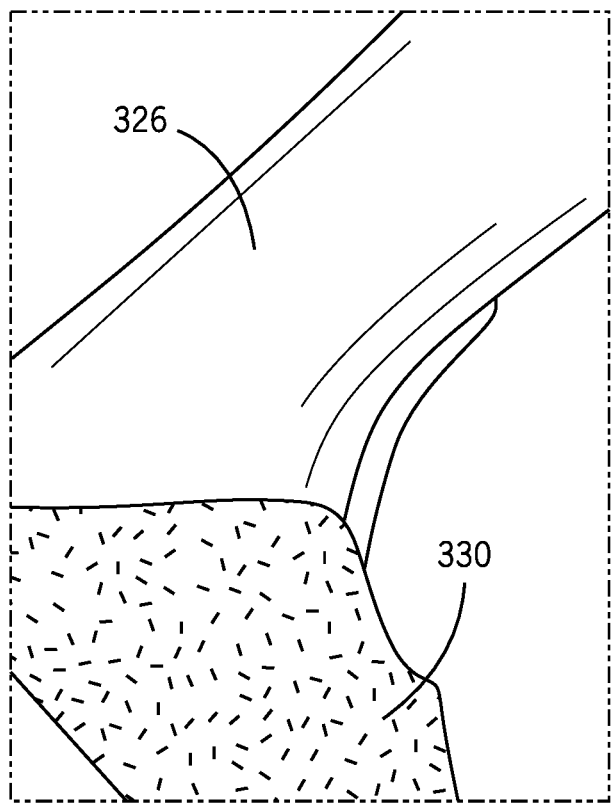

An example procedure for layering carbon fiber to form the second embodiment of the outer brace 200 is as follows. As seen in FIGS. 11-13, a first layer of bi-directional, pre-impregnated carbon fiber 330 can be molded or wrapped around portions of the dummy mold that will ultimately be covered by the outer brace 200. Since the pre-impregnated carbon fiber 330 is often sticky due to the resin, the layers 330 tend to wrap easily around the dummy mold 326 and tend to stick well to successive layers of carbon fiber 330. As a note, other types of carbon fiber 330 are useable within this process and are not limited to bi- or uni-directional, pre-impregnated carbon fiber. Next in the process, a first layer of uni-directional, pre-impregnated carbon fiber 330 can be molded or wrapped to the first layer of bi-directional carbon fiber 330. Again, a second layer of bi-directional, pre-impregnated carbon fiber 330 can be molded or wrapped to the first layer of uni-directional carbon fiber 330. Thus, the three layers of carbon fiber form a sandwich with two layers of bi-directional carbon fiber 330 on the outsides and a single layer of uni-directional carbon fiber 330 in the middle. Carbon fiber can be layered on portions of the foot, ankle, and heel, as well as layered in a similar manner around the calf area to form the calf-cuff member. While the layers of carbon fiber are described as being a sandwich construction of two layers of bi-directional carbon fiber with a single layer of uni-directional carbon fiber, other combinations are possible. For example, another combination of layers may include two outer layers of bi-directional carbon fiber 330 with two inner layers of uni-directional carbon fiber 330. This method of layering up carbon fiber may be equally applicable to construction of the first embodiment of the outer brace 100, described previously.

For the strut member 116 of the first embodiment 100, a strip of uni-directional, pre-impregnated carbon fiber 330 that is sandwiched between two layers of bi-directional, pre-impregnated carbon fiber 330 can be positioned between the carbon fiber on the heel to the carbon fiber on the calf-cuff member 118. The strip can be about ⅝ inch wide to about 1 inch wide depending on the strength and/or flexibility requirements of the strut member 116, which may be affected by the size and activity level of the patient. Alternatively, the strip can be other widths as necessitated by the requirements of the AFO. In certain embodiments, the coupling of the strut member 116 to the calf-cuff 118 and/or the heel-end portion of the lower support member 102 can be accomplished by positioning the strut member 116 between layers of carbon fiber on the respective calf-cuff member 118 and/or heel-end portion of the lower support member 102. For example, the heel-end portion of the lower support member 102 may include two inner layers of uni-directional, pre-impregnated carbon fiber sandwiched between two outer layers of bi-directional, pre-impregnated carbon fiber and the strut member may be positioned between the two inner layers of uni-directional carbon fiber.

Figure 14:
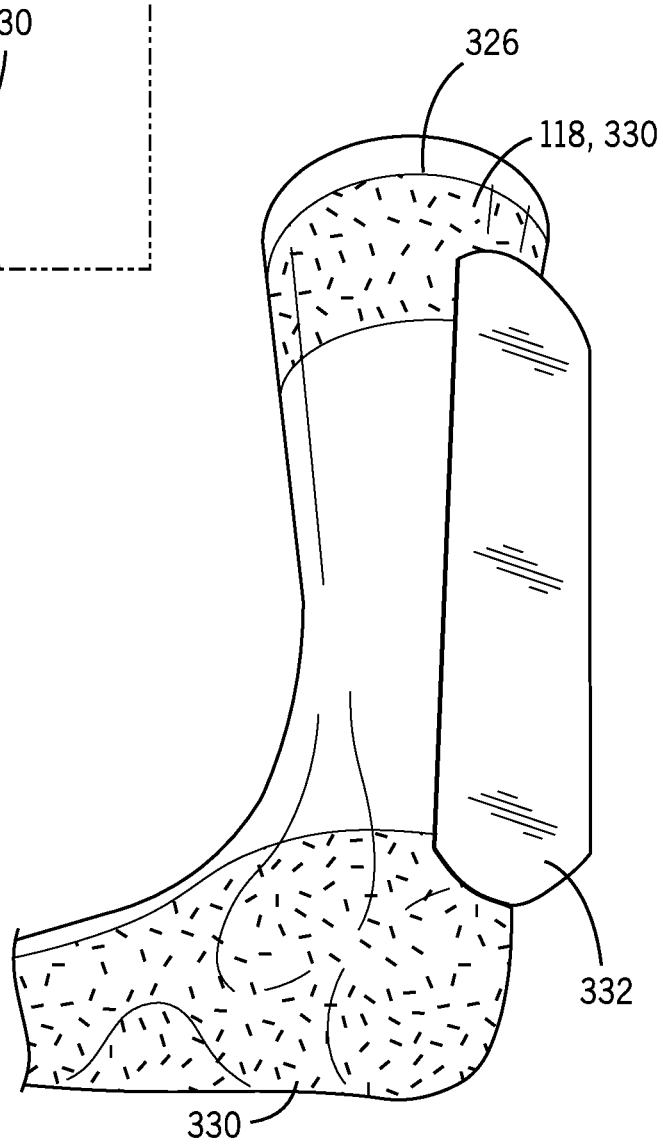
FIG. 14 is a view of the dummy mold with a thin layer of thermoplastic positioned over the location of the strut member (not shown)

As seen in FIG. 14, once the strut member 116 (obscured by the thermoplastic 332 in FIG. 14) is coupled to both the calf-cuff member 118 and the heel-end portion of the lower support member 102, a thin layer of thermoplastic 332 is positioned over the strut member 116 [Block 510]. The layer of thermoplastic may be about 1/32 inch thick and may be slightly wider than the strut member 116. The thin layer of thermoplastic 332 will mold with the strut member 116 and will provide additional stability to the strut member 116.

Next, a layer of plastic wrap (not shown), or similar material, is wrapped over the layers of carbon fiber 330 and the thin layer of thermoplastic 332 [Block 520]. The plastic wrap ensures that the outer surface of the carbon fiber 330, once baked, will have a smooth coating. In addition to the plastic wrap, the entire assembly including the dummy mold 326, carbon fiber 330, and the thin layer of thermoplastic 332 may be sealed in a vacuum sealed bag (not shown) [Block 530]. The next step is to put the dummy mold 326, carbon fiber 330, thin layer of thermoplastic 332, plastic wrap, and vacuum sealed bag in an oven to bake [Block 540]. Oven temperature of about 250 degrees Fahrenheit should be sufficient to bake both the carbon fiber 330 and the thin layer of thermoplastic 332.

Once the baking process is complete, the carbon fiber 330 and thin layer of thermoplastic 332 can be removed from the dummy mold 326 and plastic wrap [Block 550]. At this point and as seen in FIGS. 15-17, the strut member 116 or, more particularly, the edges of the thin thermoplastic 332 can be trimmed and the carbon fiber 330 on the calf-cuff member 118 and the lower support member 102 can be trimmed to the shape identified in FIG. 2A-2D [Block 560].

Figure 18:
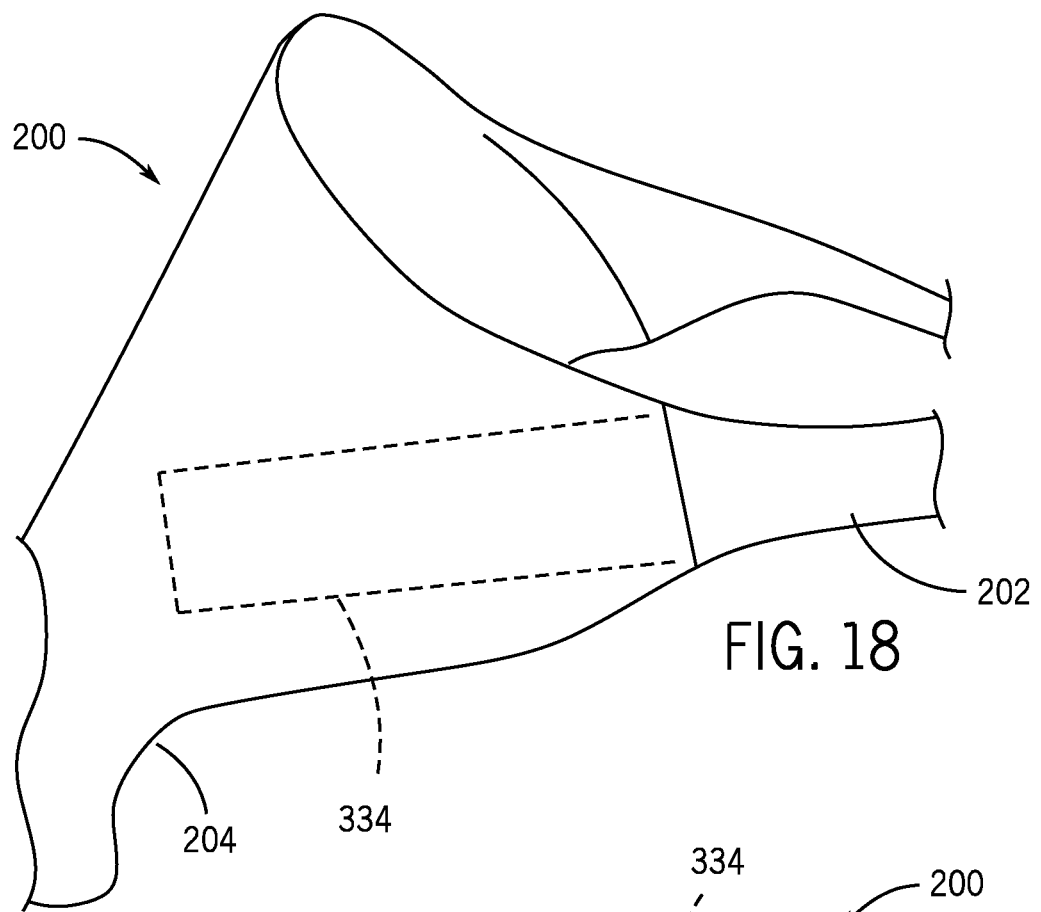
FIG. 18 is a close-up view of the back of the calf-cuff member of the second embodiment of the outer brace.
Figure 19:
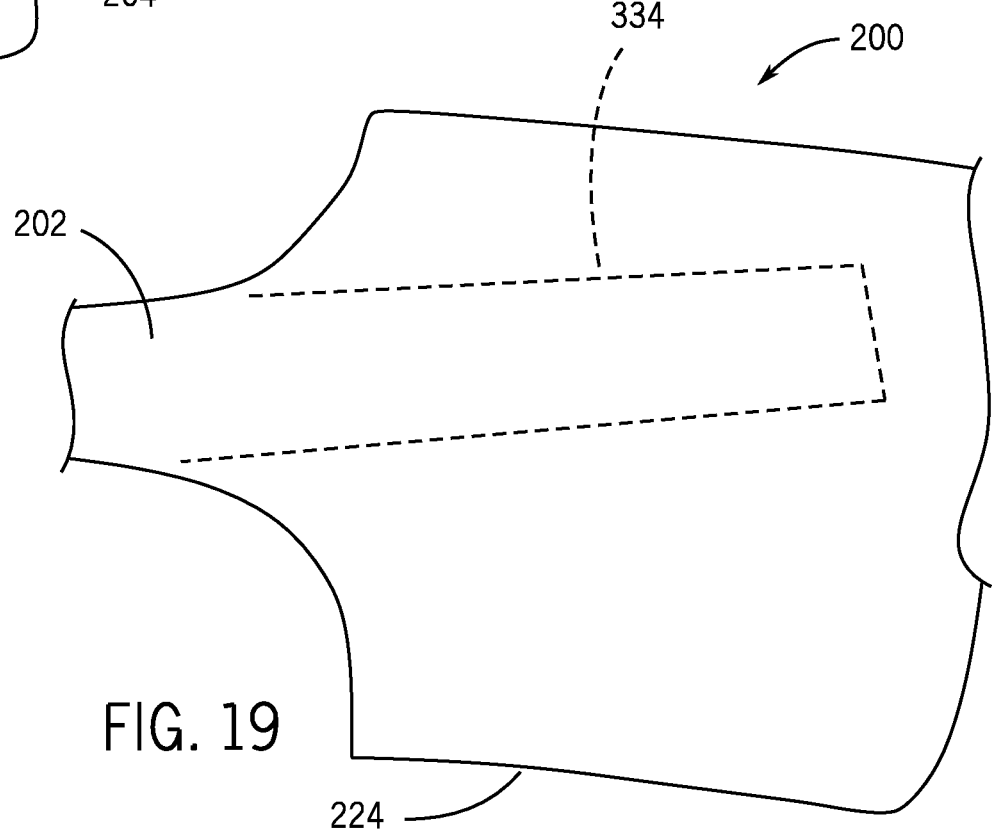
FIG. 19 is a close-up view of the lower support member of the second embodiment of the outer brace.
Figure 22:
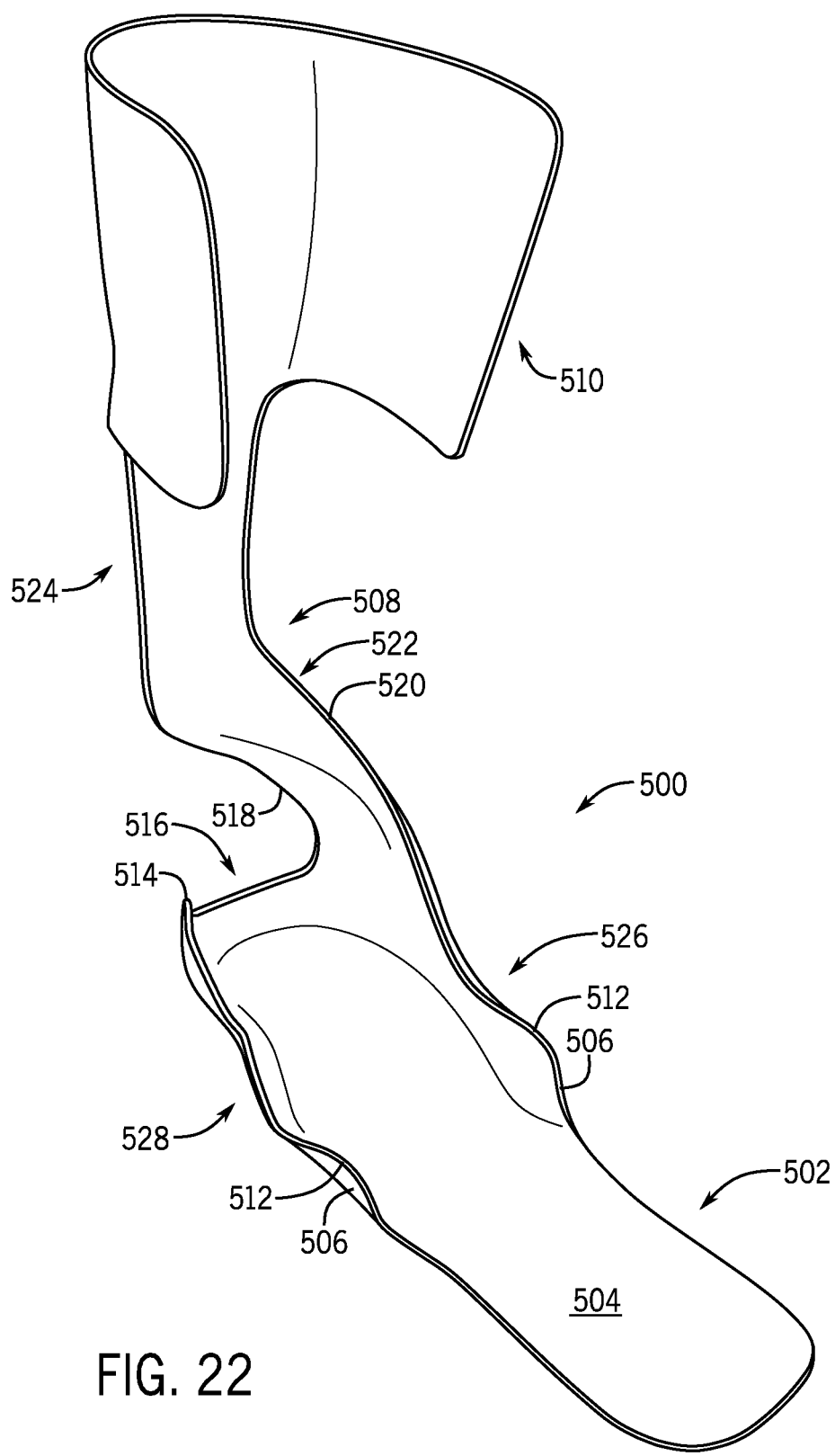
FIG. 22 is a front perspective view of a fourth embodiment of an outer brace of an AFO.

Now that a description of manufacturing the first embodiment of the outer brace 100 is complete, reference will now be made to FIGS. 18-19 and [Blocks 600-670] in discussing the steps of manufacturing the second embodiment of the outer brace 200.

Referring to FIGS. 5 and 9, after the inner brace shell 322 is manufactured [Blocks 450-460], these steps are repeated a second time to form a second inner brace shell [Block 600]. It is noted that the modified plaster mold 316 is not subsequently modified in this embodiment of the outer brace 200 to include the flat posterior section. Once the second inner brace shell is removed from the modified plaster mold 316, the second inner brace shell is not cut to shape according to FIG. 2. Rather, the second inner brace shell is used to layer-up sheets or layers of carbon fiber 330 to form the second embodiment of the outer brace 200. In this step, layers of carbon fiber 330 are first laid up on the foot plate 208, sidewall areas 212, and calf-cuff 224 of the second inner brace shell to form the lower support member 204 and the calf-cuff member 224 [Block 610]. It is noted that the heel-end portion of the second inner brace shell is not wrapped in carbon fiber 330 (i.e., to make room for the large calcaneus opening 220). As seen in FIG. 1, the heel-end portion 206 of the outer brace 200 remains open. Alternatively, the heel-end portion 206 of the second inner brace shell may be wrapped with carbon fiber 330 and subsequently cut-down after the outer brace 200 is baked in the oven.

To couple the calf-cuff member 224 and the lower support member 204 a pair of strut members 202 is formed by using fiberglass and resin 334. While various types of fiberglass 334 may be used, fiberglass "G-braid" may be used in this application along with an epoxy resin. In particular, epoxy resin is added to strips of fiberglass 334 and the strips of fiberglass 334 are laid on the second inner brace shell with the respective ends of the strips protruding into each of the calf-cuff member 224 and the lower support member 204 [Block 620]. Each of the strips of fiberglass 334 extends into the lower support member 204 at an approximate 45 degree angle, as shown by the dotted lines in FIG. 18. As the strips of fiberglass 334 extend upwards towards the calf-cuff member 224, the strips overlap at about a mid-point between the calf-cuff member and the lower support member 204. And, as seen by the dotted lines in FIG. 19, the combined strips of fiberglass 334 extend into the calf-cuff member 224 about ½ to about ¾ of the way up the calf-cuff member 224. As discussed with respect to the first embodiment of the outer brace 100, the strut members 202 may extend into the respective calf-cuff member 224 and lower support member 204 between layers of the carbon fiber 330.

Once the carbon fiber 330 and the fiberglass 334 are wrapped around the second inner brace shell, a thin layer of plastic wrap (not shown), or similar material, is wrapped over the assembly [Block 630]. Next, the entire assembly including the second inner brace shell, carbon fiber 330, fiberglass 334 and the plastic wrap may be sealed in a vacuum sealed bag [Block 640]. The next step is to put the entire assembly, including the vacuum sealed bag, in an oven to bake [Block 650]. After baking in the oven for a sufficient time to harden the material, the carbon fiber and fiberglass can be separated from the second inner brace shell and plastic wrap [Block 660]. Finally, portions of the strut members 202, the calf-cuff member 224, and the lower support member 204 may be trimmed to the shape identified in FIG. 1 [Block 670].

Referring to FIG. 20-21, a third embodiment of an outer brace 400 for an AFO is shown. As seen in the figures, the outer brace 400 includes a lower support member 402 that is similar to the previous embodiments of the outer brace 100, 200. That is, the lower support member 402 includes a foot plate 404 having opposing sidewall members 406 with a mid-foot raised edge 412 extending proximally from a mid-region of the foot plate 404. The outer brace 400 in FIGS. 20-21 is different from previous embodiments in that it includes a helical or spiral shaped strut member 408 that extends superiorly or upward from one of the side wall member 406 (i.e., the strut member 408 may extend from a medial or lateral side of the foot plate 404). On one of the medial or lateral sides of the foot plate 404, the mid-foot raised edge 412 extends proximally and transitions into an edge 420 of the strut member 408. As the strut member 408 extends upward, it spirals or wraps around a posterior or heel side of the brace 400 and couples to or transitions to a shin-cuff member 410 that wraps around and supports an anterior side of a patient's front part of the leg or shin area. As an example, if the strut member 408 extends upward from a medial side of the foot plate 404, the strut member 408 will wrap around the heel side and couple or transition to the shin-cuff member 410 on the lateral side of the patient. The side wall member 406 that does not couple to or transition to the strut member 408 includes a posterior raised edge 414 that wraps around the heel portion 416 of the lower support member 402 and transitions into another edge 418 of the strut member 408. The strut member 408 defines a gap, opening, or open area between the foot plate 404 and the edge 418 of the strut member 408 directly upward or superior from the foot plate 404 such that the patient's heel area is substantially unobstructed by a portion of the brace 400 on the heel side.

As with other embodiments, the shin-cuff member 410 may include a fastener mechanism such as a VELCRO® strap that couples the shin-cuff member 410 to the patient's leg. The outer brace 400 shown in FIGS. 20 and 21 may be used on a patient's left or right leg, and in certain embodiments, the outer brace 400 may be mirrored for the patient's opposite leg such that the strut member 408 extends from opposite side wall members 406 of each respective foot's brace.

The outer brace 400 may be constructed in similar ways as the previously described embodiments of the outer brace 100, 200. That is, the brace 400 may be constructed of carbon fiber and/or fiberglass using the previously described methods. Additionally, the strut member 408 may be of a substantially constant or uniform width between the edges 418, 420 during the extension from the foot plate 404 to the shin-cuff member 410 of about 1 inch, 1.5 inches, 2 inches, 2.5 inches, or 3 inches, among other possible widths. In certain embodiments, the width may be any possible width between about 0.5 inch to about 4 inches.

Referring to FIG. 22-26, a fourth embodiment of an outer brace 500 for an AFO is shown. As seen in the figures, the outer brace 500 includes a lower support member 502 that includes a foot plate 504 having opposing sidewall members 506 with a mid-foot raised edge 512 extending proximally from a mid-portion of the foot plate 504. The outer brace 500 in FIGS. 22-26 is different from previous embodiments in that it includes a single, curved strut member 508 that extends superiorly or upward from the side wall member 506 on the medial side 526 of the foot plate 504. That is, there is no strut member extending from a lateral side 528 of the foot plate. It is noted that while the strut 508 is described as coupling or transitioning from a medial side 526 of the foot plate 504, in certain instances, the strut member 508 may alternatively couple or transition from a lateral side 528 of the foot plate 504 without departing from the teachings of the present disclosure.

As seen in FIGS. 22-26, the curved strut member 508 includes an inferior or lower section 522 that is curved and that couples with the foot plate 504 at the medial side 526. The curved strut member 508 also includes a superior or upper section 524 that is generally straight and that couples with a calf-cuff member 510 on a posterior side. The mid-foot raised edge 512 on the medial side 526 extends proximally and transitions into an edge 520 of the strut member 508 at the lower section 522. As the strut member 508 extends upward from the foot plate 504, it curves around a posterior or heel side of the brace 500. The curved lower section 522 transitions to the generally straight upper section 524 above a heel region to be occupied by the heel portion of an inner brace 530, shown in broken line in FIG. 25. Above the heel region, the strut member 508 extends upward or superiorly to the calf-cuff member 510 on a posterior side.

Figure 25:
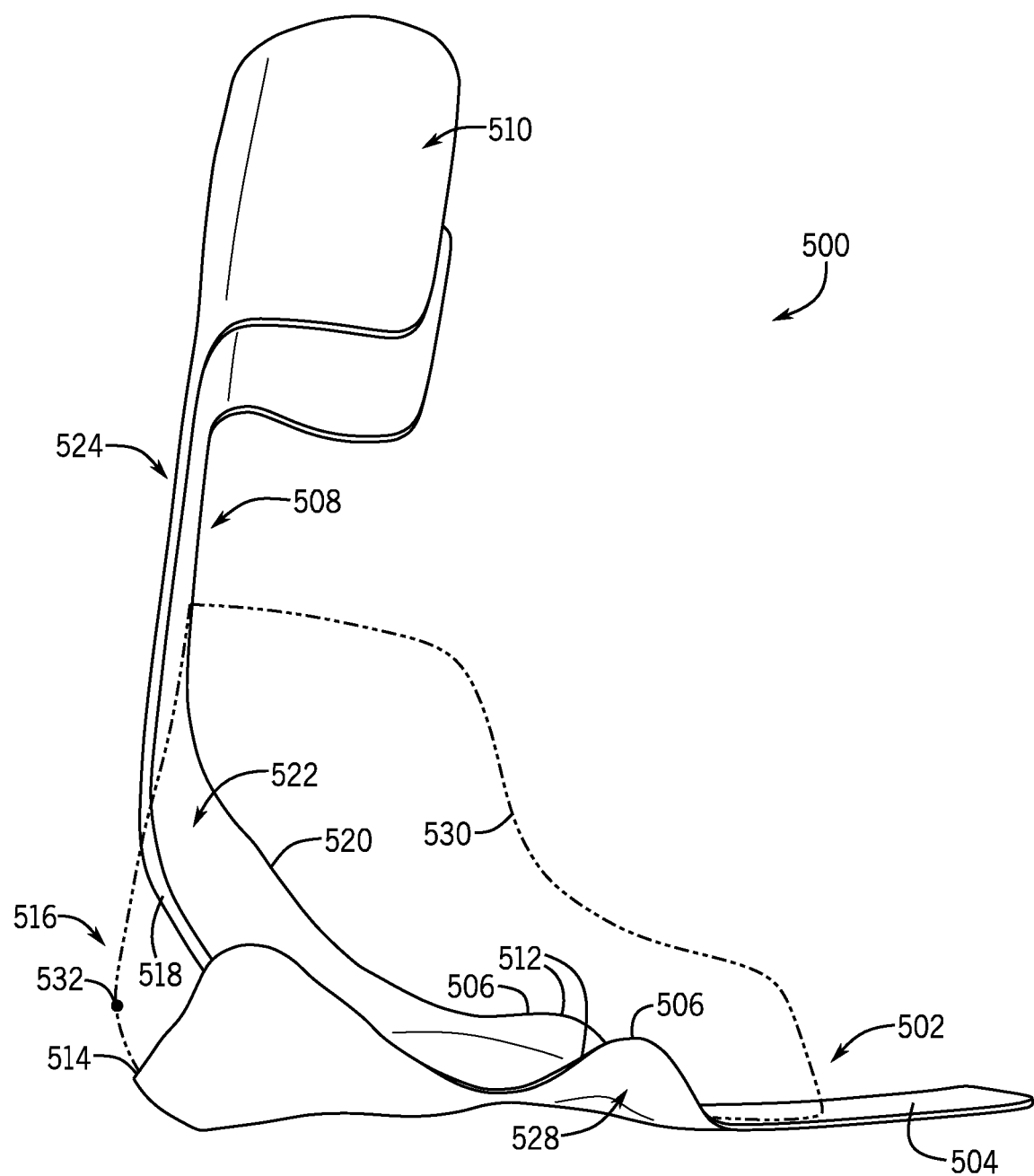
FIG. 25 is a lateral side view of the fourth embodiment of the outer brace of FIG. 22.
Figure 26:
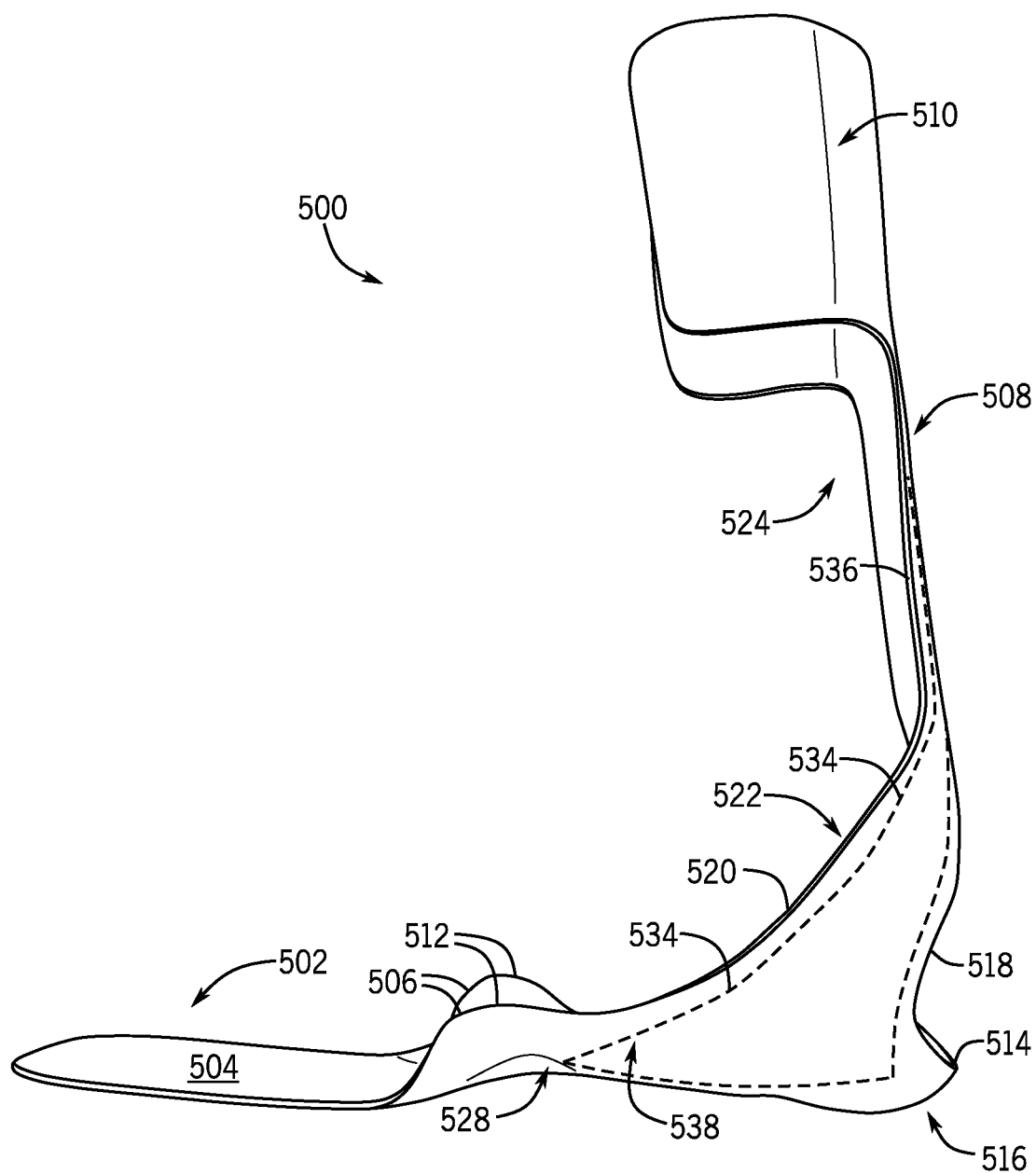
FIG. 26 is a medial side view of the fourth embodiment of the outer brace of FIG. 22.

Stated differently, the curved strut member 508 couples with the foot plate 504 at an arch region 538 of the plate 504, as seen in FIG. 26, while leaving open the heel side of the foot plate 504 so as to allow the inner brace 530, as seen in FIG. 25, to occupy the heel side of the foot plate 504 without being encumbered by the strut member 508. In this way, the strut member 508 may be positioned over the patient's medial malleolus while curving around and superior to the calcaneus and, in particular, the point where the calcaneus meets the calcaneal tendon. From the point superior to the calcaneus, the strut member 508 extends linearly in a superior direction to the calf-cuff member 510.

The calf-cuff member 510 wraps around the posterior, medial, and lateral sides of the patient's leg or calf area. The calf-cuff member 510 is open on an anterior side, allowing the patient to position his or her leg therethrough.

As illustrated in FIGS. 22-26, the side wall member 506 on the lateral side 528 does not couple to or transition to the strut member 508. Instead, a posterior raised edge 514 of the side wall member 506 on the lateral side 528 wraps around a heel portion 516 of the lower support member 502 and transitions into a lateral edge 518 of the strut member 508. The lower section 522 of the strut member 508 defines a gap, opening, or open area between the foot plate 504 and the edge 518 of the strut member 508 directly upward or superior from the foot plate 504 such that the patient's heel area is substantially unobstructed by a portion of the brace 500 on the heel side.

As seen in FIG. 25, which is a side view of the outer brace 500 from the lateral side 528 showing an inner brace 530 in broken line, the gap or open area between the foot plate 504 and the lateral edge 518 of the strut member allows for the inner brace 530 to be positioned within the outer brace 500 and to be seated such that a most posterior point 532 on either of the combined inner/outer brace 530, 500 is on the inner brace 530. Since the patient wears the AFO including both the inner and outer braces 530, 500 inside a shoe, the cumulative size of the inner and outer braces of the AFO affects the size of shoe the patient can wear. Thus, having the most posterior point 532 located on the inner brace 530 means the patient only has to compensate additional shoe sizes for the inner brace 530 in a lengthwise direction (heel-to-toe). That is, if the most posterior point 532 were to be on the outer brace 500, the patient would likely have to compensate shoe sizes for the thicknesses of both the inner and outer braces 530, 500 in the lengthwise direction. In this way, keeping the heel area open allows for the inner brace 530 to be positioned more posteriorly or towards the heel area such that it sits more posterior than the outer brace 500.

As with other embodiments, the calf-cuff member 510 may include a fastener mechanism such as a VELCRO® strap that couples the calf-cuff member 510 to the patient's leg. The outer brace 500 shown in FIGS. 22-26 may be used on a patient's right leg and, in certain instances, the outer brace 500 for the patient's left leg may be mirrored where the medial and lateral sides 526, 528 are opposite to that shown in FIGS. 22-26.

Regarding manufacturing, the outer brace 500 may be constructed in similar ways as the previously described embodiments of the outer brace 100, 200, 400. That is, the brace 500 may be constructed of carbon fiber and/or fiberglass using the previously described methods. Additionally, the strut member 508 may be of a substantially constant or uniform width between the edges 518, 520 during the extension from the foot plate 504 to the calf-cuff member 510 of about 1 inch, 1.5 inches, 2 inches, 2.5 inches, or 3 inches, among other possible widths. In certain embodiments, the width may be any possible width between about 0.5 inch to about 4 inches.

Figure 23:
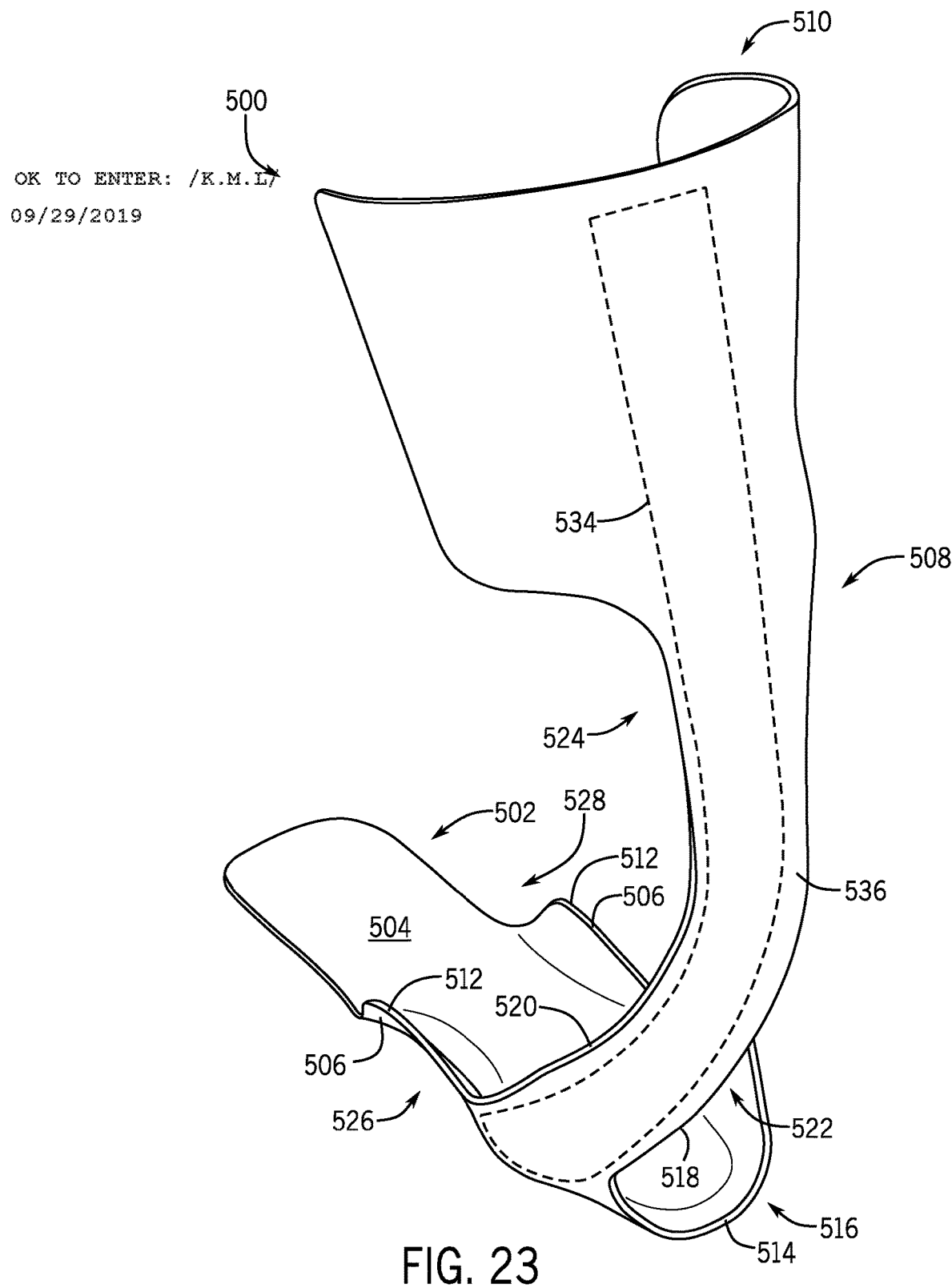
FIG. 23 is a back perspective view of the fourth embodiment of the outer brace of FIG. 23.
Figure 24:
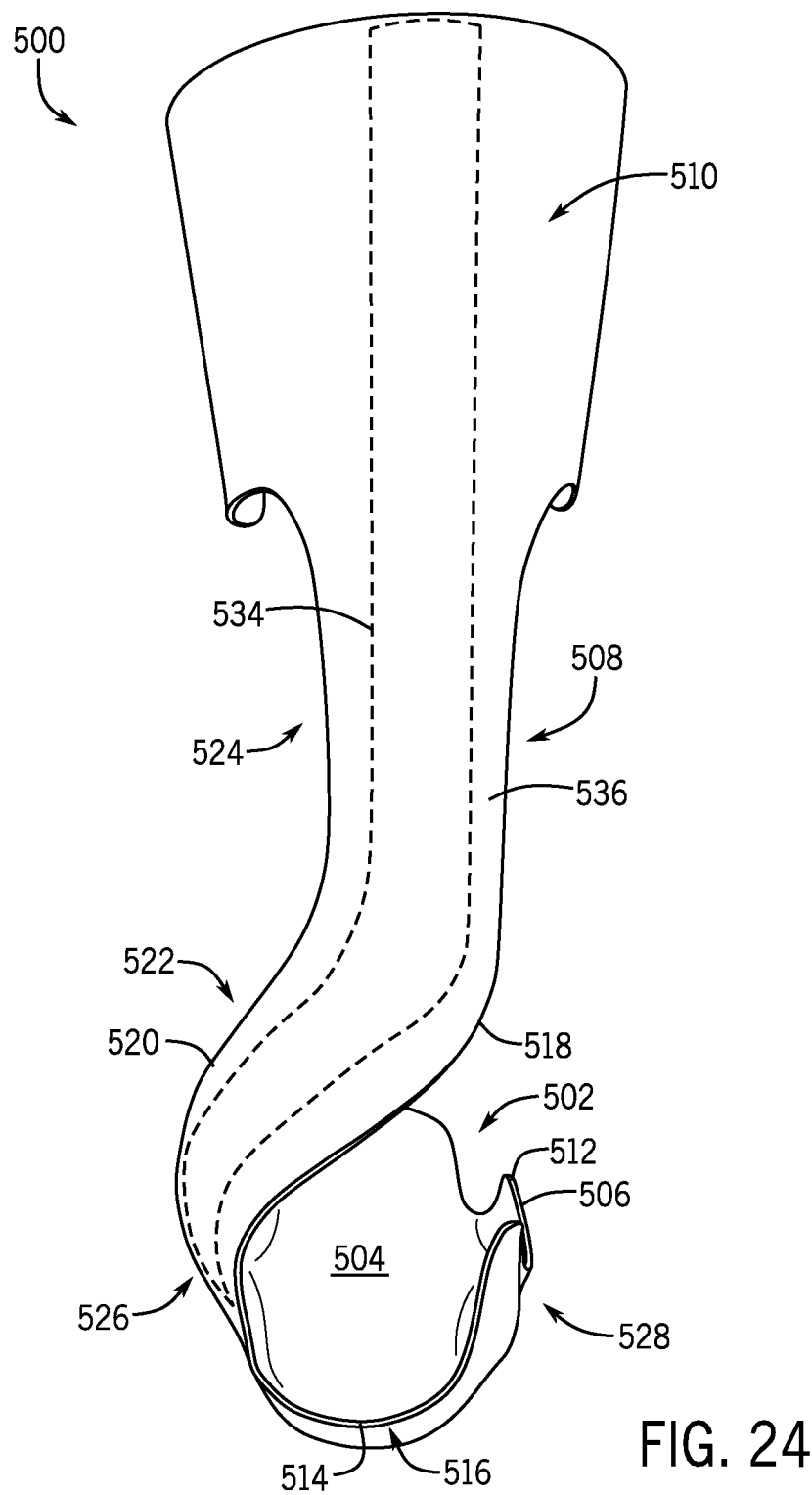
FIG. 24 is a back view of the fourth embodiment of the outer brace of FIG. 22.

In certain instances, as seen in FIGS. 23-24 and 26, the strut 508 may include an inner strut member 534 (shown in broken line) sandwiched within an outer strut member 536. The inner and outer strut members 534, 536 may, for example, be formed by layering up a first set of carbon fiber layers, positioning a central carbon fiber band on the first set of carbon fiber layers, and then layering up a second set of carbon fiber layers (similar to the first set of carbon fiber layers) to sandwich the central carbon fiber band. In this example, the central carbon fiber band is the inner strut member 534 and the first and second carbon layers are the outer strut member 536. In certain instances, the inner strut member 534 may be about ⅝ inch wide. In certain embodiments, the inner strut member 534 may be any width between about ¼ inch wide to about 1 inch wide.

As seen in FIG. 26, which is a side view of the outer brace 500 from the medial side 526, the inner strut member 534 may be fanned out, feathered, or widened at an arch region 538 near the foot plate 504. That is, the width of the inner strut member 534 at the arch region 538 may be wider than the inner strut member 534 at other portions of the strut member 508. The inner strut member 534 being wide at the arch region 538 provides strength and rigidity to the outer brace 500 since flexing of the outer brace 500 occurs throughout the arch region 538 and lower section 522 of the strut member 508.

Patients requiring an AFO often over-pronate, which means their feet roll inward and onto the arches of the foot. Providing strength and rigidity on the medial side 526 at the arch region 536 concentrates the material of the brace 500 at the area where the patient is most likely to pressure or stress the brace 500. And since the brace 500 is needed to provide arch support for the inner brace 530, shown in broken line in FIG. 25, the arch region 538 is ideally situated for the positioning of a wider portion of the inner strut member 534.

The outer brace 500 can be manufactured as described with reference to the previous embodiments of the outer brace 100, 200, 400. In certain instances, the step of modifying the modified plaster mold by adding additional material (e.g., plaster) to the posterior side of the modified plaster mold to form a second modified plaster mold at [Block 480] of FIG. 4 may also include adding plaster to the along the medial side 526 at the arch region 536. The additional material is added and flattened, as opposed to allowing a patient specific contour to remain. The flattening of this area facilitates forming a strut member 508 with a flat inner surface that extends from the foot plate 504 to the calf-cuff member 510. Forming a flat strut member 508, as opposed to a patient specific contouring strut member, may ensure uniform mechanical characteristics of the strut member 508. Otherwise, a strut member 508 that is contoured to the patient's anatomy could exhibit stress concentrations that affect performance of the AFO. After forming the second modified plaster mold, the manufacturing process continues as described previously.

An exemplary construction of the outer brace 500, at Block [500] of FIG. 4, may include the following layers of material from inside to outside: resin; fabric (e.g., suede-type fabric); thermoplastic; multiple layers of carbon fiber (e.g., alternate layers of bi-directional and uni-directional carbon fiber); polyethylene; fabric; and, resin. Other arrangements of layers are possible and contemplated herein.

Although various representative embodiments of this invention have been described above with a certain degree of particularity, those skilled in the art could make numerous alterations to the disclosed embodiments without departing from the spirit or scope of the inventive subject matter set forth in the specification. All directional references (e.g., top, bottom, front, back) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ankle-foot orthosis for a lower leg including a calf, ankle, and foot of a patient, the ankle-foot orthosis comprising:
    a foot plate comprising a toe side, a heel side opposite the toe side, a medial side including an arch region, and a lateral side opposite the medial side;
    a calf-cuff member configured to abut the calf of the patient; and
    a support member extending between the foot plate and the calf-cuff member, the support member consisting of a strut member including a curved lower section and a straight upper section, the curved lower section extending from the arch region of the medial side of the foot plate to a posterior position above the heel side of the foot plate, the curved lower section transitioning to the straight upper section at the posterior position, the straight upper section extending superiorly to the calf-cuff member, wherein a heel portion of an inner brace positioned within the ankle-foot orthosis extends further posteriorly than any portion of the ankle-foot orthosis.

2. The ankle-foot orthosis of claim 1, wherein the strut member is constructed of carbon fiber.

3. The ankle-foot orthosis of claim 2, wherein the strut member is constructed of layers of bi-directional and uni-directional carbon fiber.

4. A method of manufacturing a custom ankle-foot orthosis for a patient's lower leg and foot, the method comprising:
    forming an inner brace from molding a first material over a first portion of a positive mold of the patient's lower leg and foot;
    modifying the positive mold to form a modified positive mold, wherein modifying the positive mold to form the modified positive mold comprises forming a flattened portion of the positive mold; and
    forming an outer brace by molding at least one second material over a second portion of the modified positive mold.

5. The method of claim 4, wherein the first material is a thermoplastic material.

6. The method of claim 4, wherein the at least one second material comprises carbon fiber.

7. The method of claim 6, wherein the at least one second material further comprises a thermoplastic material.

8. The method of claim 4, wherein the positive mold comprises a cast of the patient's lower leg and foot.

9. The method of claim 4, wherein modifying the positive mold to form the modified positive mold comprises removing custom contouring aspects of the positive mold.

10. The method of claim 4, wherein the flattened portion of the positive mold comprises a band extending from a posterior region to a medial arch region.

11. The method of claim 4, wherein the outer brace comprises a foot plate, a calf-cuff member, and a strut member coupled between the foot plate and the calf-cuff member, the flattened portion of the positive mold comprise an area to which the strut member is molded.

12. The method of claim 11, wherein the outer brace incudes only one strut member comprising the strut member.

* * * * *